US012749577B2

(12) United States Patent
Olson et al.

(10) Patent No.: US 12,749,577 B2
(45) Date of Patent: Sep. 29, 2026

(54) CONTINUOUS GLUCOSE MONITORING FOLLOWER AND SOCIAL SUPPORT ENHANCEMENTS

(71) Applicant: Dexcom, Inc., San Diego, CA (US)

(72) Inventors: Carly Rose Olson, San Diego, CA (US); Afshan A. Kleinhanzl, San Diego, CA (US); Adam G. Noar, San Diego, CA (US); Harry Shaw Strothers, San Diego, CA (US); Andrew Merrill Terry, San Diego, CA (US); Michiko Araki Kelley, San Diego, CA (US); Afsaneh Sofia Sadri, San Diego, CA (US); Amit Premal Joshipura, San Diego, CA (US); Benjamin E. West, San Diego, CA (US); Apurv U. Kamath, San Diego, CA (US); Michele Leah Cambou, San Diego, CA (US); Alexander Michael Diener, San Diego, CA (US); Stacey Lynne Fischer, San Diego, CA (US); Douglas S. Kanter, San Diego, CA (US); Mark Derdzinski, Aliquippa, PA (US); Chad M. Patterson, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 72 days.

(21) Appl. No.: 18/544,919

(22) Filed: Dec. 19, 2023

(65) Prior Publication Data

US 2024/0203584 A1 Jun. 20, 2024

Related U.S. Application Data

(60) Provisional application No. 63/476,142, filed on Dec. 19, 2022.

(51) Int. Cl.
*G16H 40/67* (2018.01)

(52) U.S. Cl.
CPC .................................. *G16H 40/67* (2018.01)

(58) Field of Classification Search
None
See application file for complete search history.

(56) References Cited

U.S. PATENT DOCUMENTS

| | | | | |
|---|---|---|---|---|
| 8,406,206 B2 | 3/2013 | Chiang | | |
| 9,393,699 B1 * | 7/2016 | Jules | B25J 9/1656 | |
| 2009/0227855 A1 * | 9/2009 | Hill | A61M 5/14244 | 700/282 |
| 2010/0304674 A1 * | 12/2010 | Kim | H04W 76/10 | 455/41.2 |
| 2015/0052582 A1 * | 2/2015 | Chow | H04L 51/046 | 726/3 |
| 2016/0081134 A1 * | 3/2016 | Chow | G06F 16/337 | 455/419 |

(Continued)

FOREIGN PATENT DOCUMENTS

| | | |
|---|---|---|
| CN | 102315864 A | 1/2012 |
| JP | 6697052 B2 | 5/2020 |

*Primary Examiner* — Robert A Sorey
(74) *Attorney, Agent, or Firm* — Patterson + Sheridan, LLP

(57) ABSTRACT

Techniques for enhancing sharing of a user's analyte data and techniques for enhancing social support provided to users for managing users' health are disclosed.

20 Claims, 17 Drawing Sheets

(56) References Cited

U.S. PATENT DOCUMENTS

| | | | | |
|---|---|---|---|---|
| 2016/0127354 | A1* | 5/2016 | Borchardt | H04L 63/0823 726/10 |
| 2018/0020329 | A1* | 1/2018 | Smith | H04W 4/08 |
| 2018/0172664 | A1* | 6/2018 | Love | G16H 40/67 |
| 2021/0105885 | A1* | 4/2021 | Van Den Berg | H05B 47/19 |
| 2022/0022030 | A1* | 1/2022 | Kumar | H04L 63/0442 |
| 2022/0400986 | A1* | 12/2022 | Khanal | A61B 5/6833 |
| 2024/0137604 | A1* | 4/2024 | Kim | H04N 21/43637 |
| 2024/0146996 | A1* | 5/2024 | Shao | H04N 21/4122 |

* cited by examiner

900

900

1000

CONTINUOUS GLUCOSE MONITORING FOLLOWER AND SOCIAL SUPPORT ENHANCEMENTS

CROSS-REFERENCE TO RELATED APPLICATIONS

This application claims priority to and benefit of U.S. Provisional Application No. 63/476,142, filed Dec. 19, 2022, which is assigned to the assignee hereof and hereby expressly incorporated by reference herein in its entirety as if fully set forth below and for all applicable purposes.

BACKGROUND

Diabetes is a metabolic condition affecting hundreds of millions of people. For these people, monitoring blood glucose levels and regulating those levels to be within an acceptable range is important not only to mitigate long-term issues such as heart disease and vision loss, but also to avoid the effects of hyperglycemia and hypoglycemia. Maintaining blood glucose levels within an acceptable range can be challenging, as glucose levels are almost constantly changing over time and in response to everyday events, such as eating or exercising. Advances in medical technologies have enabled development of various systems for monitoring blood glucose, including continuous glucose monitoring (CGM) systems, which measure and record glucose concentrations in substantially real-time. CGM systems are important tools for users of these systems to ensure that measured glucose values are within the acceptable range.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

Certain aspects described herein provide a computer-implemented method. The computer-implemented method is performed by a first display device for communicating analyte data. The computer-implemented method includes obtaining analyte data from an analyte monitoring device. The computer-implemented method also includes detecting that the first display device has lost connectivity with a server computing system. The computer-implemented method also includes, in response to detecting that the first display device has lost connectivity with the server computing system: automatically initiating a scan for one or more display devices; upon detecting, based on the scan, a second display device of the one or more display devices that is in proximity to the first display device, establishing a communication link with the second display device; and transmitting the analyte data to the second display device.

Certain aspects described herein provide a computer-implemented method. The computer-implemented method includes receiving an indication that a display device associated with a user has relinquished management of transmission of analyte data from the display device. The computer-implemented method also includes in response to receiving the indication, managing transmission of analyte data from the display device for a predetermined amount of time.

Certain aspects described herein provide a first display device. The first display device includes at least one processor and a memory. The memory stores instructions, which when executed by the at least one processor, perform an operation. The operation includes obtaining analyte data from an analyte monitoring device. The operation also includes detecting that the first display device has lost connectivity with a server computing system. The operation in response to detecting that the first display device has lost connectivity with the server computing system: automatically initiating a scan for one or more display devices; upon detecting, based on the scan, a second display device of the one or more display devices that is in proximity to the first display device, establishing a communication link with the second display device; and transmitting the analyte data to the second display device.

DETAILED DESCRIPTION OF CERTAIN INVENTIVE ASPECTS

Figure 1:
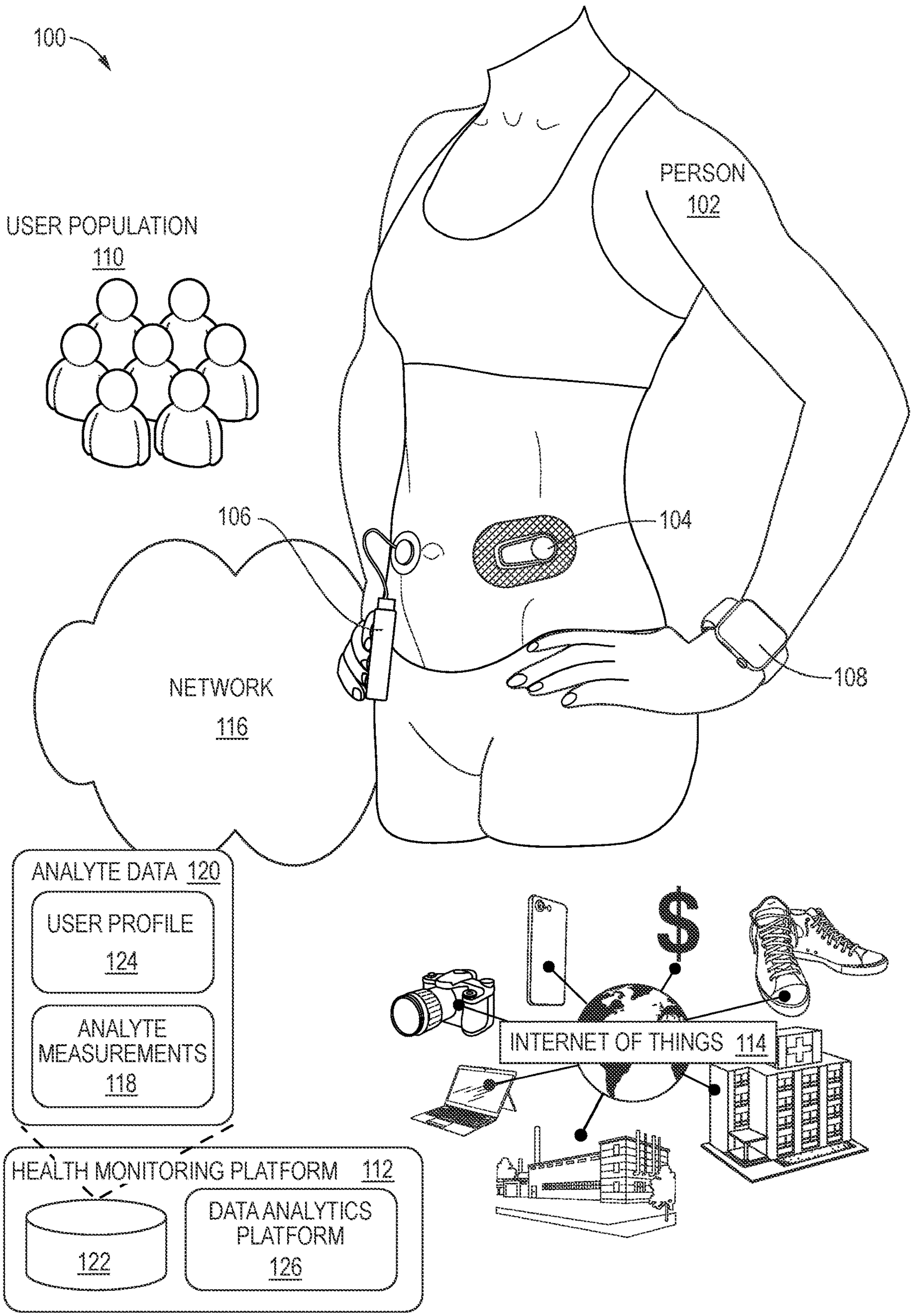
FIG. 1 illustrates an example environment in which a medical support system can be implemented, according to certain aspects described herein.

In a CGM system, a glucose sensor measures glucose levels of a patient and communicates the raw sensor measurements to a transmitter, which can then transmit corresponding glucose values to the patient's display device, such as a mobile phone. The patient can use their display device to monitor the patient's health and collect patient health data.

Additionally, current research has shown that patients with CGM systems can benefit from having social support that helps the patient manage their health and medical conditions, such as diabetes. For example, patients with social support can have a better experience with CGM systems, better self-management, and better health outcomes than patients without social support. Such social support can involve, for example, providing emotional and mental support, monitoring the patient's glucose data (and/or other health data), encouraging the patient to meet milestones or challenges related to diabetes management, and the like.

Consequently, many applications are being developed to provide social support services to patients with certain medical conditions, such as diabetes. An exemplary analyte monitoring application (e.g., CGM application) that provides social support services can allow a patient to share their glucose data with one or more other users (also referred to herein as followers or supporters). For example, the patient can invite, via the analyte monitoring application, one or more supporters to download an analyte monitoring application on the supporter's computing device (e.g., mobile phone). A supporter that receives the invite can accept the invitation, download the analyte monitoring application, and use the analyte monitoring application to monitor the patient's glucose data. For example, the analyte monitoring application can allow the supporter to view the patient's glucose data in (near) real-time, receive alerts when the patient's glucose values meet a predetermined condition (e.g., exceeds a first threshold or drops below a second threshold), and the like.

However, while such analyte monitoring applications allow supporters to view a patient's glucose data, technical challenges still exist.

First, in some instances, the patient's display device (running an analyte monitoring application) is unable to share the patient's glucose data with a supporter's display device (running an analyte monitoring application). For example, currently, to share the patient's glucose data with a supporter, the patient's CGM transmitter will transmit the patient's glucose data to the patient's display device (e.g., mobile device). The patient's display device will then transmit the patient's glucose data to a cloud server for storage using a cellular communication connection or WiFi communication connection. The cloud server can then forward the patient's glucose information to the supporter's display device, allowing the supporter to view the patient's glucose data substantially in real-time. However, when the patient's display device loses internet connectivity or is otherwise unable to connect to a cloud server associated with the analyte monitoring application, the patient's display device is not able to transmit the patient's glucose data to the cloud server. As a result, the supporter's display device is not able to receive the patient's (updated) glucose data. The patient's display device can lose internet connectivity due to the patient's display device being in a particular location with a lack of (or limited) internet coverage (e.g., campground, airplane, ocean, etc.). In other instances, the patient's display device is unable to connect to the cloud server (even if the patient's display device has internet connectivity) when there is a server-side failure or a communication problem associated with the analyte monitoring application.

The inability to share glucose data when the patient's display device loses internet connectivity can compromise the patient's health. For example, if the patient's display device loses internet connectivity or is otherwise unable to share the patient's glucose data when the patient is experiencing a hypoglycemic episode or hyperglycemic episode, then the patient's display device is unable to notify the supporter, and the supporter is unable to help the patient in the event of the hypoglycemic episode or hyperglycemic episode.

Second, in certain environments, such as a hospital, a medical professional (e.g., doctor, nurse, etc.) is responsible for taking care of multiple patients utilizing CGM sensors for glucose monitoring. Currently, however, it can be significantly difficult for a medical professional to gain access to and view each patient's glucose information from that patient's CGM sensor. For example, with certain existing analyte monitoring applications, each patient would have to send a separate invite to each medical professional in order to share the patient's data with that medical professional.

Third, certain existing analyte monitoring applications can be configured to share the patient's glucose data, but is not able to share other types of analyte data, such as the patient's insulin data. In some cases, providing the patient's glucose data alone without other types of analyte data is insufficient to convey the full context regarding the patient's medical condition (e.g., diabetes). For instance, providing the patient's glucose data without the patient's insulin data can be insufficient to convey to the supporter whether the patient is experiencing insulin resistance (e.g., due to high insulin levels), pancreatitis (e.g., due to low insulin levels), etc.

To address the aforementioned technical challenges associated with sharing a patient's glucose data, certain aspects herein describe various enhancements to sharing patient data.

In certain aspects described below, the enhancements to sharing patient data include enabling an analyte monitoring application (running on a patient's display device) to send the patient's data (e.g., including analyte data, such as glucose data) to one or more supporters in proximity to the patient in the event the patient's display device loses internet connectivity (e.g., cellular connectivity, WiFi connectivity, etc.).

Additionally, in certain aspects described below, the enhancements to sharing the patient's data include at least one of (i) allowing the analyte monitoring application to provide various types of patient data, such as various types of analyte data (e.g., insulin data), in addition to glucose data, to one or more supporters, (ii) allowing the analyte monitoring application to directly send the patient's data to one or more devices in an environment, such as a hospital, (iii) allowing the analyte monitoring application to use other processes (as opposed to an invitation process) (e.g., email links, etc.) to share the patient's data, (iv) allowing certain supporters (e.g., parents or guardians) to restrict modification of sharing permissions on a patient's (e.g., child's) analyte monitoring application, (v) allowing certain supporters to untether a display device from receiving information from the patient's analyte monitoring application, etc.

Certain aspects also provide various enhancements to providing social support services to a patient via an analyte monitoring application. The various enhancements include a set of features that aims to (i) help supporters better understand the patient's CGM experience, (ii) enhance engagement with CGM systems for both patients and their supporters through common games and challenges, (iii) help facilitate positive and productive discussions between patients and their supporters, (iv) help identify positive moments/achievements and facilitate sharing such positive moments/achievements with supporters, or (v) enable supporters to acknowledge a patient's progress with managing their health.

The techniques described herein for providing enhancements to sharing of a patient's data are described more fully herein with respect to FIGS. 1-11 below. Note that although certain aspects herein are described with respect to the management of diabetes, a CGM system, a CGM application, and the transmission of analyte measurements between devices, the protocols and techniques described herein are similarly applicable to any type of health management system that includes any type of analyte sensor (e.g., lactate sensor, ketone sensor, etc.), any type of health management application, and/or transmission of any type of analyte data. Additionally, note that, hereinafter, although certain aspects described herein refer to an analyte monitoring device performing various techniques described herein for transmitting analyte data, it is the transmitter in the analyte monitoring device that performs the various techniques described herein for transmitting analyte data.

FIG. 1 is an illustration of an environment 100 in an example implementation that is operable to employ techniques as described herein. The illustrated environment 100 includes person 102, who is depicted wearing a (wearable) analyte monitoring device 104, medicament delivery system 106, and display device 108. The illustrated environment 100 also includes other users in a user population 110 of the analyte monitoring device, health monitoring platform 112, and Internet of Things 114 (IoT 114). The analyte monitoring device 104, medicament delivery system 106, display device 108, user population 110, health monitoring platform 112, and IoT 114 are communicatively coupled, one to another, via a network 116.

Alternately or additionally, one or more of the analyte monitoring device 104, the medicament delivery system 106, and the display device 108 can be communicatively coupled in other ways, such as using one or more short range communication protocols or techniques. For example, the analyte monitoring device 104, the medicament delivery system 106, and the display device 108 can communicate with one another using one or more of Bluetooth (including e.g., Bluetooth Low Energy (BLE)), near-field communication (NFC), 5G, and so forth. The analyte monitoring device 104, the medicament delivery system 106, and the display device 108 can leverage these types of communication to form a closed-loop system between one another. In this way, the medicament delivery system 106 can deliver a medicament (e.g., insulin) based on predictions of an analyte level (e.g., glucose level) computed in real-time (e.g., by the display device 108) as analyte measurements are obtained by the analyte monitoring device 104.

In certain aspects, the analyte monitoring device 104 is a CGM device. As used herein, the term "continuous" when used in connection with analyte monitoring refers to an ability of a device to produce measurements substantially continuously, such that the device can be configured to produce the analyte measurements at regular or irregular intervals of time (e.g., approximately every hour, approximately every 30 minutes, approximately every 5 minutes, and so forth), responsive to establishing a communicative coupling with a different device (e.g., when the display device 108 establishes a wireless connection with the analyte monitoring device 104 to retrieve one or more of the measurements), and so forth. This functionality along with further aspects of the configuration of the analyte monitoring device 104 are discussed in more detail in relation to FIG. 2.

In certain aspects, the analyte monitoring device 104 transmits the analyte measurements 118 to one or more of the display device 108, the medicament delivery system 106, or some other device, such as via Bluetooth. The analyte monitoring device 104 can communicate these measurements in real-time, e.g., as they are produced using an analyte sensor. Alternately or in addition, the analyte monitoring device 104 can communicate the analyte measurements 118 at set time intervals, e.g., every 30 seconds, every minute, every 5 minutes, every hour, every 6 hours, every day, and so forth. Further still, the analyte monitoring device 104 can communicate these measurements responsive to a request for the measurements, e.g., communicated to the analyte monitoring device 104 when the display device 108 causes display of a user interface having information about the person 102's glucose level, updates such a display, predicts the person 102's upcoming glucose level for the purpose of delivering insulin, and so forth. Accordingly, the display device 108 can maintain the analyte measurements 118 of the person 102 at least temporarily, e.g., in computer readable storage media of the display device 108.

Although illustrated as a wearable device (e.g., a smart watch), the display device 108 can be configured in a variety of ways without departing from the spirit or scope of the described techniques. By way of example and not limitation, the display device 108 can be configured as a different type of mobile device (e.g., a mobile phone or tablet device). In one or more implementations, the display device 108 can be configured as a dedicated device associated with the health monitoring platform 112, e.g., with functionality to obtain the analyte measurements 118 from the analyte monitoring device 104, perform various computations in relation to the analyte measurements 118, display information related to the analyte measurements 118 and the health monitoring platform 112, communicate the analyte measurements 118 to the health monitoring platform 112, and so forth. In contrast to implementations where the display device 108 is configured as a mobile phone, however, in some aspects, the display device 108 does not include some functionality available with mobile phone or wearable configurations when configured as a dedicated analyte monitoring device, such as the ability to make phone calls, camera functionality, the ability to utilize social networking applications, and so on.

Additionally, the display device 108 can be representative of more than one device in accordance with the described techniques. In one or more scenarios, for instance, the display device 108 can correspond to both a wearable device (e.g., a smart watch) and a mobile phone. In such scenarios, both of these devices can be capable of performing at least some of the same operations, such as to receive the analyte measurements 118 from the analyte monitoring device 104, communicate them via the network 116 to the health monitoring platform 112, display information related to the analyte measurements 118, and so forth.

Alternately or in addition, different devices can have different capabilities that other devices do not have or that are limited through computing instructions to specified devices. In the scenario where the display device 108 corresponds to a separate smart watch and a mobile phone, for instance, the smart watch can be configured with various sensors and functionality to measure a variety of physiological markers (e.g., heartrate, breathing, rate of blood flow, and so on) and activities (e.g., steps) of the person 102. In this scenario, the mobile phone is not configured with these sensors and functionality or can include a limited amount of that functionality—although in other scenarios a mobile phone is able to provide the same functionality. Continuing with this particular scenario, the mobile phone can have capabilities that the smart watch does not have, such as an amount of computing resources (e.g., battery and processing speed) that enables the mobile phone to more efficiently carry out computations in relation to the analyte measurements 118. Even in scenarios where a smart watch is capable of carrying out such computations, computing instructions can limit performance of those computations to the mobile phone so as not to burden both devices and to utilize available resources efficiently. To this extent, the display device 108 can be configured in different way and represent different numbers of devices than discussed herein without departing from the spirit and scope of the described techniques.

As mentioned above, the display device 108 communicates the analyte measurements 118 to the health monitoring platform 112. In the illustrated environment 100, the analyte measurements 118 are shown stored in storage device 122 of the health monitoring platform 112 as part of analyte data 120. The storage device 122 can represent one or more databases and also other type of storage capable of storing the analyte data 120. The analyte data 120 also includes user profile 124. In accordance with the described techniques, the person 102 corresponds to a user of at least the health monitoring platform 112 and can also be a user of one or more other, third-party service providers. To this end, the person 102 can be associated with a username and be required, at some time, to provide authentication information (e.g., password, biometric data, and so forth) to access the health monitoring platform 112 using the username. This information can be captured in the user profile 124. The user profile 124 can also include a variety of other information about the user, such as demographic information describing the person 102, information about a health care provider, payment information, prescription information, determined health indicators, user preferences, account information for other service provider systems (e.g., a service provider associated with a wearable, social networking systems, and so on), and so forth. The user profile 124 can include different information about a user within the spirit and scope of the described techniques.

Further, the analyte data 120 not only represents data of a user that corresponds to the person 102, but also represents data of the other users in the user population 110. Given this, the analyte measurements 118 in the storage device 122 include the analyte measurements from an analyte sensor of the analyte monitoring device 104 worn by the person 102 and also include analyte measurements from analyte sensors of analyte systems worn by persons corresponding to the other users in the user population 110. It follows also that the analyte measurements 118 of these other users are communicated by their respective devices via the network 116 to the health monitoring platform 112 and that these other users have respective user profiles 124 with the health monitoring platform 112.

The data analytics platform 126 represents functionality to process the analyte data 120 to generate a variety of predictions, such as by using various machine learning models. Based on these predictions, the health monitoring platform 112 can provide recommendations and/or other information about the predictions. For instance, the health monitoring platform 112 can provide the recommendations or other information directly to the user, to a medical professional associated with the user, and so forth. Although depicted as separate from the display device 108, portions or an entirety of the data analytics platform 126 can alternately or additionally be implemented at the display device 108. The data analytics platform 126 is also configured to generate these predictions using data in addition to the analyte measurements 118, such as additional data obtained via the IoT 114.

It is to be appreciated that the IoT 114 represents various sources capable of providing data that describes the person 102 and the person 102's activity as a user of one or more service providers and activity with the real world. By way of example, the IoT 114 can include various devices of the user, e.g., cameras, mobile phones, laptops, and so forth. To this end, the IoT 114 can provide information about interaction of the user with various devices, e.g., interaction with web-based applications, photos taken, communications with other users, and so forth. The IoT 114 can also include various real-world articles (e.g., shoes, clothing, sporting equipment, appliances, automobiles, etc.) configured with sensors to provide information describing behavior, such as steps taken, force of a foot striking the ground, length of stride, temperature of a user (and other physiological measurements), temperature of a user's environment, types of food stored in a refrigerator, types of food removed from a refrigerator, driving habits, and so forth. Additionally, the IoT 1114 can include various devices (e.g., mesh devices) capable of communicating with one or more of the analyte monitoring device 104, display device 108, and health monitoring platform 112 via one or more communication protocols, such as Bluetooth, WiFi, cellular communications, etc.

The IoT 114 can also include third parties to the health monitoring platform 112, such as medical providers (e.g., a medical provider of the person 102) and manufacturers (e.g., a manufacturer of the analyte monitoring device 104, the medicament delivery system 106, or the display device 108) capable of providing medical and manufacturing data, respectively, that can be leveraged by the data analytics platform 126. Certainly, the IoT 114 can include devices and sensors capable of providing a wealth of data in connection with recommendations based on analyte monitoring (e.g., continuous glucose monitoring) without departing from the spirit or scope of the described techniques. In the context of measuring an analyte, e.g., continuously, and obtaining data describing such measurements, consider the following discussion of FIG. 2.

Figure 2:
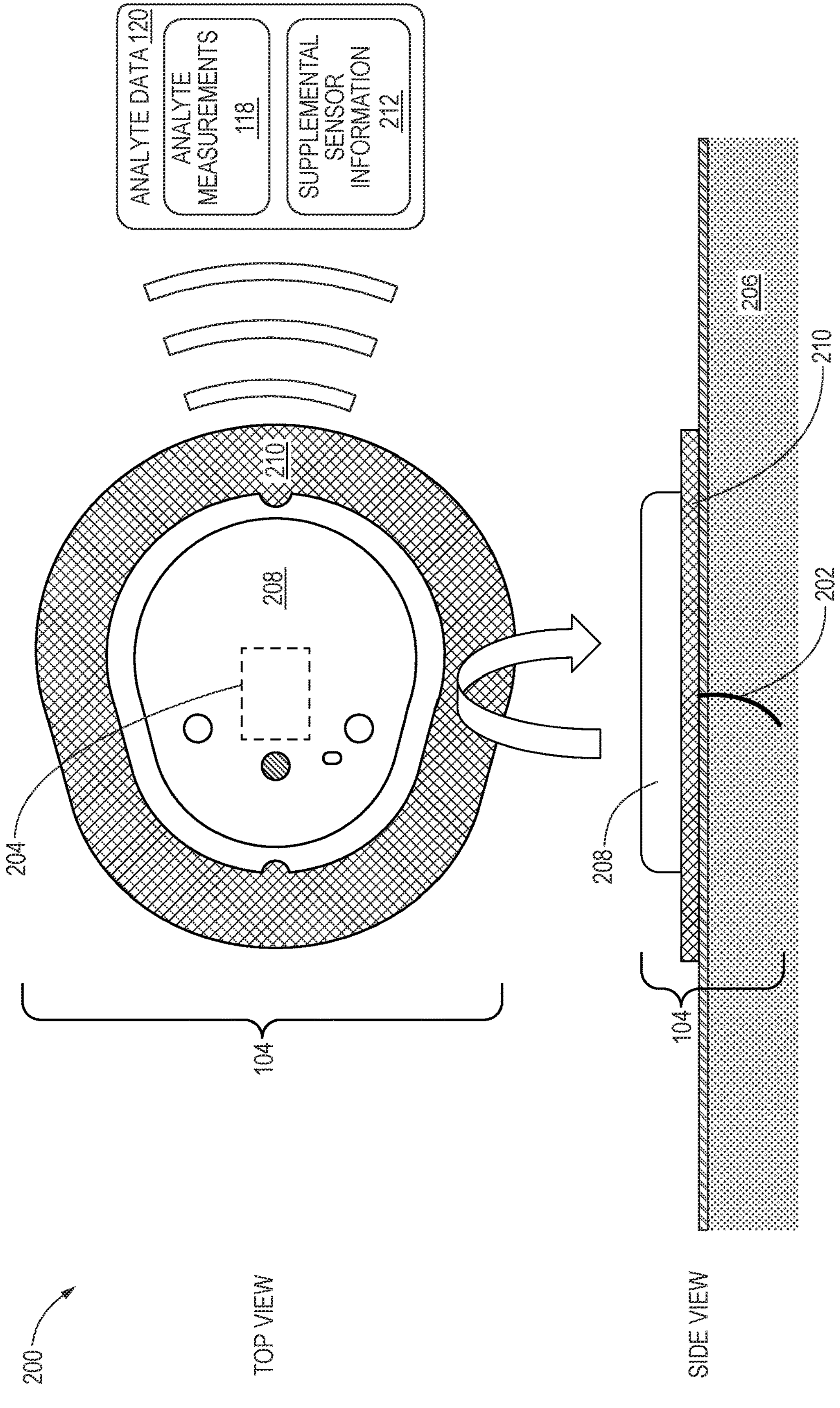
FIG. 2 illustrates an example analyte monitoring device, according to certain aspects described herein.

FIG. 2 depicts an example 200 of an implementation of the analyte monitoring device 104 of FIG. 1 in greater detail, according to certain aspects. In particular, the illustrated example 200 includes a top view and a corresponding side view of the analyte monitoring device 104. It is to be appreciated that the analyte monitoring device 104 can vary in implementation from the following discussion in various ways without departing from the spirit or scope of the described techniques.

In this example 200, the analyte monitoring device 104 is illustrated to include an analyte sensor 202 (e.g., a glucose sensor) and a sensor module 204. Here, the analyte sensor 202 is depicted in the side view having been inserted subcutaneously into skin 206, e.g., of the person 102. The sensor module 204 is approximated in the top view as a dashed rectangle. The analyte monitoring device 104 also includes a transmitter 208 in the illustrated example 200. Use of the dashed rectangle for the sensor module 204 indicates that it can be housed or otherwise implemented within a housing of the transmitter 208. Antennae and/or other hardware used to enable the transmitter 208 to produce signals for communicating data, e.g., over a wireless connection to the display device 108, can also be housed or otherwise implemented within the housing of the transmitter 208. In this example 200, the analyte monitoring device 104 further includes adhesive pad 210.

In operation, the analyte sensor 202 and the adhesive pad 210 can be assembled to form an application assembly, where the application assembly is configured to be applied to the skin 206 so that the analyte sensor 202 is subcutaneously inserted as depicted. In such scenarios, the transmitter 208 can be attached to the assembly after application to the skin 206 via an attachment mechanism (not shown). Alternatively, the transmitter 208 can be incorporated as part of the application assembly, such that the analyte sensor 202, the adhesive pad 210, and the transmitter 208 (with the sensor module 204) can all be applied substantially at once to the skin 206. In one or more implementations, this application assembly is applied to the skin 206 using a separate sensor applicator (not shown). Unlike the finger sticks required by conventional blood glucose meters, user-initiated application of the analyte monitoring device 104 with a sensor applicator is nearly painless and does not require the withdrawal of blood. Moreover, the automatic sensor applicator generally enables the person 102 to embed the analyte sensor 202 subcutaneously into the skin 206 without the assistance of a clinician or healthcare provider.

The analyte monitoring device 104 can also be removed by peeling the adhesive pad 210 from the skin 206. It is to be appreciated that the analyte monitoring device 104 and its various components as illustrated are simply one example form factor, and the analyte monitoring device 104 and its components can have different form factors without departing from the spirit or scope of the described techniques.

In operation, the analyte sensor 202 is communicably coupled to the sensor module 204 via at least one communication channel which can be a wireless connection or a wired connection. Communications from the analyte sensor 202 to the sensor module 204 or from the sensor module 204 to the analyte sensor 202 can be implemented actively or passively and these communications can be continuous (e.g., analog) or discrete (e.g., digital).

The analyte sensor 202 can be a device; a molecule; a chemical; a device and a molecule; a device and a chemical; a molecule and a chemical; or a molecule, a device, and a chemical which changes or causes a change in response to an event which is at least partially independent of the analyte sensor 202. The sensor module 204 is implemented to receive indications of changes to the analyte sensor 202 or caused by the analyte sensor 202. For example, the analyte sensor 202 can include glucose oxidase which reacts with glucose and oxygen to form hydrogen peroxide that is electrochemically detectable by the sensor module 204 which can include an electrode. In this example, the analyte sensor 202 can be configured as or include a glucose sensor configured to detect analytes in blood or interstitial fluid that are indicative of glucose level using one or more measurement techniques. In one or more implementations, the analyte sensor 202 can also be configured to detect analytes in the blood or the interstitial fluid that are indicative of other markers, such as lactate levels, ketones, or ionic potassium, which can improve accuracy in identifying or predicting glucose-based events. Additionally or alternatively, the analyte monitoring device 104 can include additional sensors and/or architectures to the analyte sensor 202 to detect those analytes indicative of the other markers.

In another example, the analyte sensor 202 (or an additional sensor of the analyte monitoring device 104—not shown) can include a first and second electrical conductor and the sensor module 204 can electrically detect changes in electric potential across the first and second electrical conductor of the analyte sensor 202. In this example, the sensor module 204 and the analyte sensor 202 are configured as a thermocouple such that the changes in electric potential correspond to temperature changes. In some examples, the sensor module 204 and the analyte sensor 202 are configured to detect a single analyte, e.g., glucose. In other examples, the sensor module 204 and the analyte sensor 202 are configured to use diverse sensing modes to detect multiple analytes, e.g., ionic sodium, ionic potassium, carbon dioxide, and glucose.

Alternatively or additionally, the analyte monitoring device 104 includes multiple sensors to detect not only one or more analytes (e.g., ionic sodium, ionic potassium, carbon dioxide, glucose, and insulin) but also one or more environmental conditions (e.g., temperature). Thus, the sensor module 204 and the analyte sensor 202 (as well as any additional sensors) can detect at least one of the presence of one or more analytes, the absence of one or more analytes, or changes in one or more environmental conditions. As noted above, the analyte monitoring device 104 can be configured to produce data describing a single analyte (e.g., glucose) or multiple analytes. Further, a combination of the analytes for which analyte monitoring devices are configured can vary across different lots of the monitoring devices manufactured (e.g., by the health monitoring platform 112), such that analyte monitoring devices having different architectures can be configured for use by different patient populations and/or for different health conditions.

In certain aspects, the sensor module 204 can include a processor and memory (not shown). The sensor module 204, by leveraging the processor, can generate the analyte measurements 118 based on the communications with the analyte sensor 202 that are indicative of the above-discussed changes. Based on the above-noted communications from the analyte sensor 202, the sensor module 204 is further configured to generate communicable packages of data that include at least one analyte measurement 118. In this example 200, the analyte data 120 represents these packages of data. Additionally or alternatively, the sensor module 204 can configure the analyte data 120 to include additional data, including, by way of example, supplemental sensor information 212. The supplemental sensor information 212 can include a sensor identifier, a sensor status, temperatures that correspond to the analyte measurements 118, measurements of other analytes that correspond to the analyte measurements 118, and so forth. It is to be appreciated that supplemental sensor information 212 can include a variety of data that supplements at least one analyte measurement 118 without departing from the spirit or scope of the described techniques.

In implementations where the analyte monitoring device 104 is configured for wireless transmission, the transmitter 208 can transmit the analyte data 120 as a stream of data to a computing device. Alternatively or additionally, the sensor module 204 can buffer the analyte measurements 118 and/or the supplemental sensor information 212 (e.g., in memory of the sensor module 204 and/or other physical computer-readable storage media of the analyte monitoring device 104) and cause the transmitter 208 to transmit the buffered analyte data 120 later at various regular or irregular intervals, e.g., time intervals (approximately every second, approximately every thirty seconds, approximately every minute, approximately every five minutes, approximately every hour, and so on), storage intervals (when the buffered analyte measurements 118 and/or supplemental sensor information 212 reach a threshold amount of data or a number of measurements), when requested by another device, and so forth.

Figure 3:
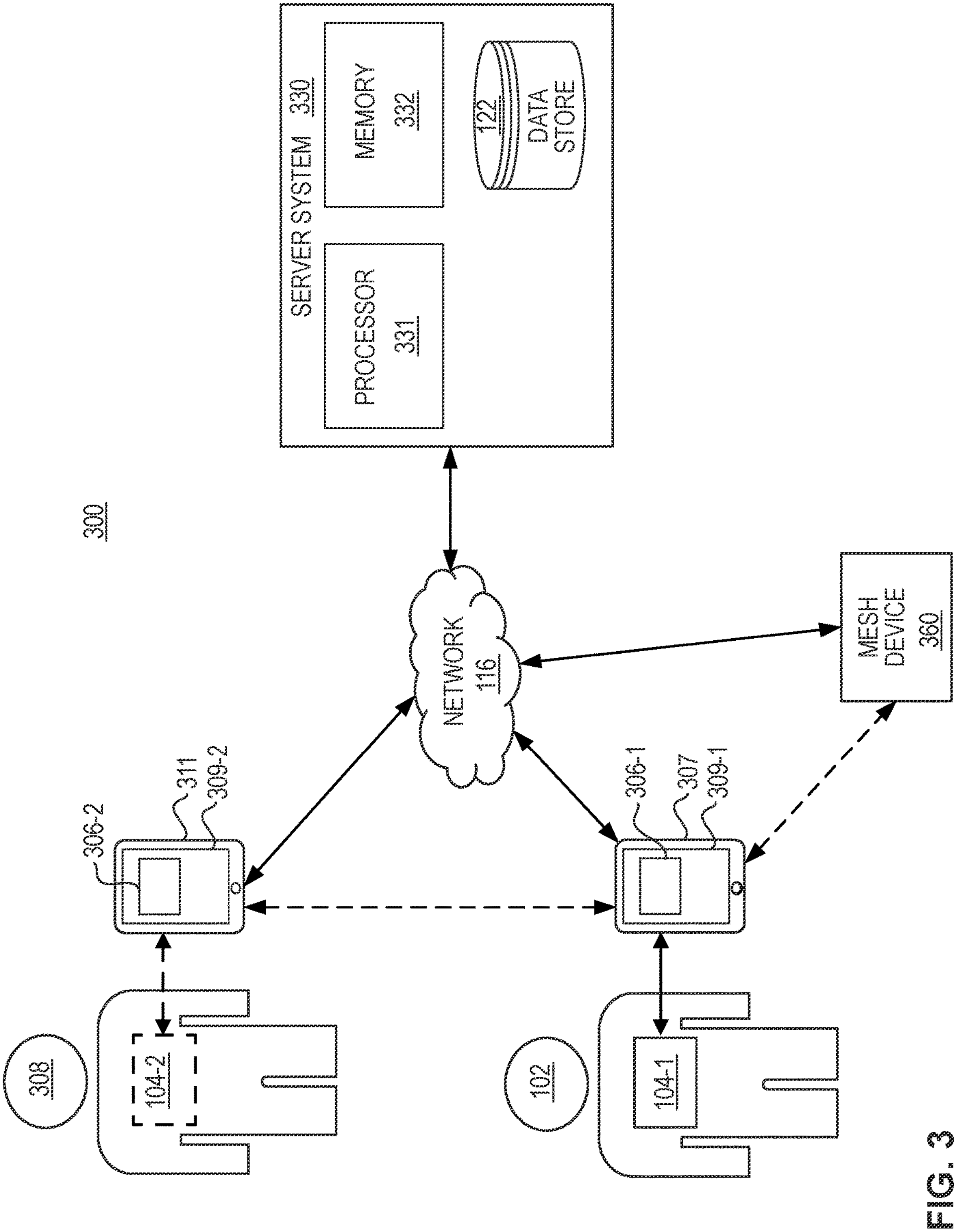
FIG. 3 illustrates an example medical support system, according to certain aspects described herein.

FIG. 3 illustrates a block diagram of an example medical support system 300 that allows for sharing a person's data (e.g., analyte data) with one or more other users (referred to herein as followers or supporters). Medical support system 300 includes an analyte monitoring device 104(*s*), a patient device 307, a supporter device 311, a mesh device 360, and a server system 330. The patient device 307, supporter device 311, and the server system 330 are interconnected via the network 116. The network 116 can be a local area network (LAN), wide area network (WAN), a cellular network, the Internet, or any other group of connected computing devices. The patient device 307 and the supporter device 311 are reference examples of the display device 108 described herein with respect to FIG. 1. The mesh device 360 is representative of a variety of devices capable of communicating via a wireless (e.g., Bluetooth, WiFi) or wired communication protocol (e.g., Ethernet). Examples of mesh devices 360 can include, but are not limited to, routers, access points, etc.

A patient (e.g., person 102) can use the patient device 307 to monitor the patient's health and collect health data. For example, the patient device 307 is communicatively coupled to the analyte monitoring device 104-1, which is configured to monitor one or more anatomical parameters of the patient, generate data as a result of the monitoring, and transmit the data to the patient device 307. In some examples, the analyte monitoring device 104-1 includes a sensor that is configured to generate measurements of one or more anatomical parameters of the patient on one or more of a continuous, periodic, or on-demand basis. For example, when the analyte monitoring device 104-1 is a CGM device, the sensor is a glucose sensor configured to measure a concentration of the patient's blood glucose. The analyte monitoring device 104-1 can transmit the measurements to the patient device 307 through a wireless (e.g., Bluetooth) or wired connection. In certain aspects, the analyte monitoring device 104-1 transmits the measurements to the patient device 307 for use by an application (e.g., application 306-1) running on the patient device 307.

The application 306 provides a user interface (UI) displaying on a display device (e.g., patient device 307, supporter device 311). For example, application 306-1 provides a UI for a display 309-1 of the patient device 307, and application 306-2 provides a UI for a display 309-2 of the supporter device 311. The display 309 can be a touchscreen display via which a user (e.g., patient or supporter) interacts with one or more of the user's display device or analyte monitoring device 104. The application 306 collects health data (e.g., from the patient, the patient's health care provider, analyte monitoring device 104, server system 330, etc.) and can display the health data via the display 309. Such health data can include, but is not limited to, patient identification information (e.g., patient's name, address, date of birth), demographic data for the patient (e.g., patient's age, body mass index (BMI), ethnicity, gender), analyte (e.g., glucose, lactate, ketone, potassium, insulin, etc.) measurements of the patient collected over time, activity data, food consumption data, metabolic rates, body temperature, heart rate, electrical cardiac activity, insulin sensitivity, insulin on board, and so forth.

The server system 330 is operable in a cloud computing environment (e.g., a private or public cloud) and can provide application services and/or features for the analyte monitoring device(s) 104 and/or application(s) 306. In certain aspects, the server system 330 is located within the health monitoring platform 112 described with respect to FIG. 1. The server system 330 can receive and store data generated by the analyte monitoring device 104 (via application 306), monitor operating parameters of the analyte monitoring device 104 (via application 306), push updates to the application 306, etc.

The server system 330 includes a processor 331 configured to execute one or more software applications stored in a memory 332. For example, the processor 331 can execute a data sharing application generally configured to enable another user (e.g., supporter 308) to receive the patient's health data and monitor the patient's health. For example, in some aspects, once the patient opts into receiving services provided by the server system 330, the server system 330 is able to receive the patient's health data transmitted by the patient device 307 and store the patient's health data in a storage system (e.g., data store 122). Once the patient opts into allowing other supporters 308 to follow the patient's health, the server system 330 can allow the supporters 308 to also access the patient's health data within the storage system.

In certain aspects, a supporter 308 uses the supporter device 311 to help the patient manage their health and medical condition, such as diabetes. Supporter device 311 can execute an application 306-2, which can access the patient's health data from at least one of server system 330 or patient device 307 and can display the patient's health data via the display 309-2. In certain aspects, the application 306-2 also receives the supporter's health data. In such aspects, the supporter device 311 can be communicatively coupled to an analyte monitoring device 104-2, which is configured to monitor one or more anatomical parameters of the supporter 308, generate data as a result of the monitoring, and transmit the data to the supporter device 311.

In certain aspects, the patient device 307 directly communicates with the supporter device 311. For example, in such aspects, the application 306-1 running on the patient device 307 can establish a Bluetooth connection with the supporter device 311, when the patient device 307 loses internet connectivity and/or is unable to connect with the server system 330. The application 306-1 can send the patient's health data to the supporter device 311 via the Bluetooth connection. The communication between a patient device 307 and one or more supporter devices 311 is described in greater detail herein.

Figure 4:
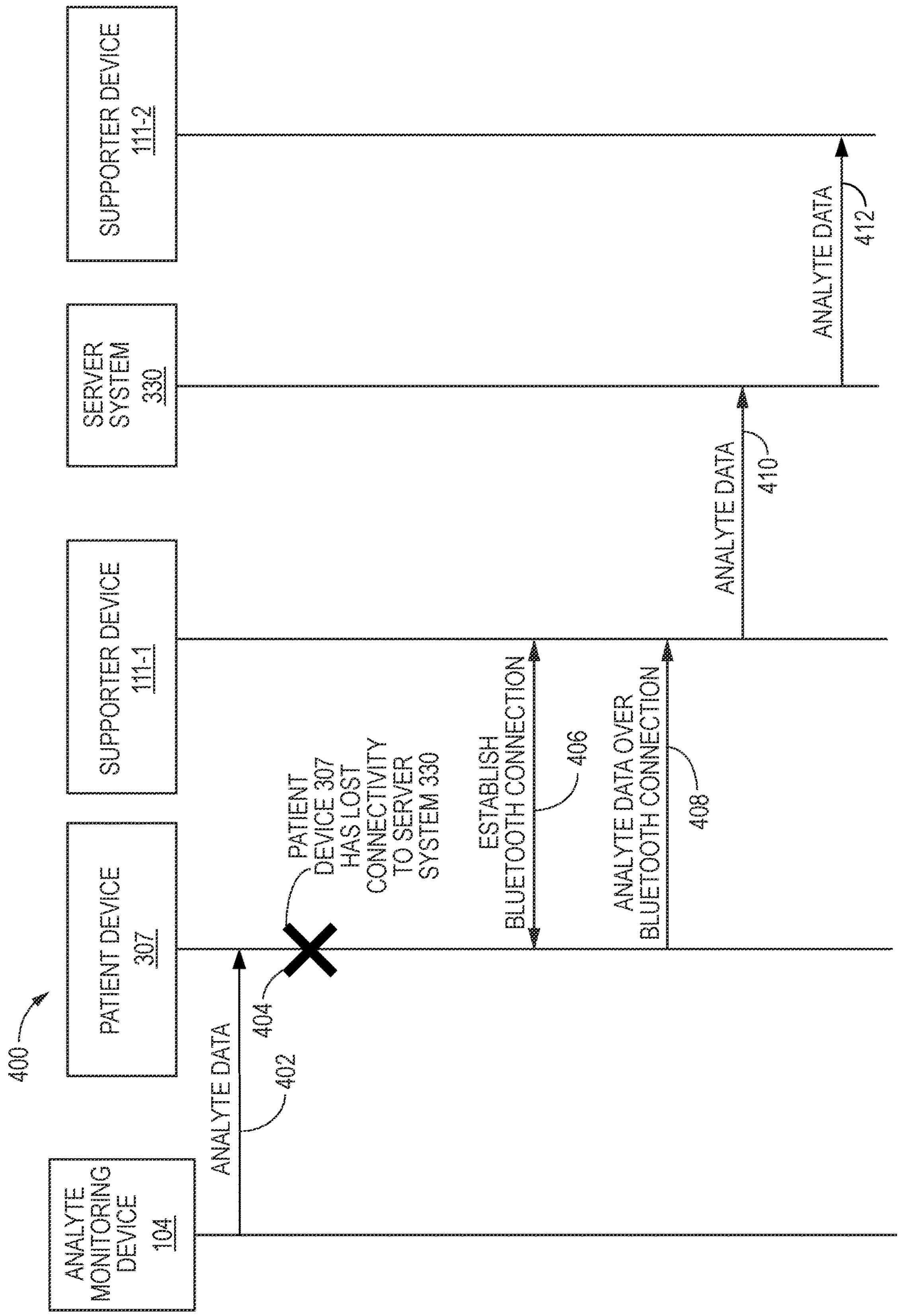
FIG. 4 is a sequence diagram illustrating example operations performed by an analyte monitoring device, a patient device, a supporter device, and a server system, according to certain aspects described herein.

FIG. 4 is a sequence diagram 400 illustrating example operations performed by an analyte monitoring device 104, a patient device 307, a supporter device 311, and a server system 330, according to certain aspects described herein. At step 402, the analyte monitoring device 104 transmits the patient's analyte data (e.g., glucose data) to the patient device 307. In certain aspects, an analyte monitoring application (e.g., application 306-1) running on patient device 307 can initially attempt to send the patient's analyte data to the server system 330 (e.g., cloud server) in order to share that data with one or more supporters 308.

In certain cases, however, the analyte monitoring application is unable to connect with the server system 330 due to the patient device 307 losing internet connectivity (e.g., cellular connectivity, WiFi connectivity, etc.), as shown in step 404. For example, the patient device 307 could be located in an environment with a lack of (or limited) internet coverage. Examples of locations with a lack of (or limited) internet coverage include, but are not limited to, remote areas (e.g., remote campgrounds), airplanes, cruise ships, etc.

Alternatively, in certain cases, the analyte monitoring application is unable to connect with the server system 330 at step 404 due to a server-side failure or malfunction that prevents the server system 330 from receiving the patient's analyte data from the analyte monitoring application. In such cases, the analyte monitoring application can determine that connectivity to the server system 330 is lost when a predetermined amount of time has elapsed since the analyte monitoring application received an acknowledgment from the server system 330.

In certain aspects, if the analyte monitoring application is unable to connect with the server system 330 for one of the aforementioned reasons, then the analyte monitoring application subsequently attempts to establish a Bluetooth connection with at least one supporter device 311 in proximity to the patient device 307. In FIG. 4, for example, at step 406, a Bluetooth connection is established between the patient device 307 and the supporter device 311-1. In certain aspects, the analyte monitoring application can attempt to establish a Bluetooth connection with a supporter device 311 on a whitelist associated with the patient device 307. In certain aspects, the whitelist can be populated with the supporter device(s) 311 of one or more supporters 308 with which the patient has a predefined relationship, such as a parent/child relationship, a familial relationship, a spousal relationship, etc.

If the whitelist is empty or a supporter device 311 on the whitelist is unavailable, then the analyte monitoring application can trigger the patient device 307 to perform a scan and prompt the patient to select, from a list of possible devices, a supporter device 111 to establish a Bluetooth connection with. A whitelist can be a data array or some other data structure maintained in memory by the patient device 307 and can include other devices with which the patient device 307 has previously paired and bonded. By adding a supporter device 311 to a whitelist, the patient device 307 and the supporter device 311 can more quickly reconnect for subsequent connections.

In certain aspects, at step 404, once a determination is made that the patient device 307 has lost internet connectivity, the patient device 307 attempts to establish a data connection to the server system 330 by implementing a connection hierarchy. For example, upon determining that the patient device 307 has lost internet connectivity via a cellular connection, the patient device 307 would attempt to establish a connection to the server system 330 via a WiFi connection at step 406. If the patient device 307 determines that a connection to the server system 330 cannot be established via a WiFi connection, then the patient device 307 would next attempt to establish a connection via Bluetooth, such as by establishing a Bluetooth connection with supporter device 311-1 at step 406. If the patient device 307 determines that a connection to the server system 330 cannot be established via a Bluetooth connection, then the patient device 307 would next attempt to establish a connection via NFC, such as by establishing a NFC connection with supporter device 311-1 at step 406.

Returning to the sequence diagram 400 of FIG. 4, at step 408, the analyte monitoring application transmits the patient's analyte data to the supporter device 311-1 via the Bluetooth connection established at step 406. At step 410, the supporter device 311-1 transmits the patient's analyte data to the server system 330. For example, there can be situations in which the patient device 307 is unable to connect to the server system 330, but the supporter device 311-1 is able to connect to the server system 330. For instance, the patient device 307 can receive internet service via a first internet service provider that does not provide coverage in the patient's location, whereas the supporter device 311-1 can receive internet service via a second internet service provider that does provide coverage in the patient's location. In such an example, the supporter device 311-1 is still be able to forward the patient's analyte data to the server system 330, allowing one or more other supporters associated with the patient to be able to view and monitor the patient's analyte data when the patient device 307 has lost internet connectivity. At step 412, for example, the server system 330 transmits the patient's analyte data to a supporter device 311-2 associated with another supporter of the patient.

Advantageously, allowing the analyte monitoring application to continue to share the patient's analyte data when the patient device 307 loses connectivity with the cloud server can allow one or more other users to help the patient in certain emergencies, including, for example, hypoglycemic episodes, hyperglycemic episodes, and the like.

Although not shown in FIG. 4, note that, in certain aspects, a patient can use a receiver (not shown) that is configured to obtain and store the patient's analyte data from the patient's analyte monitoring device. Such a receiver can lack the capability to establish a cellular connection, a WiFi connection, or a cellular connection and a WiFi connection with the server system 330. In such aspects, the patient device 307 can be configured with an analyte monitoring application that is configured to connect to the patient's receiver, gather data from the receiver, and upload the data to the server system 330.

In certain aspects, a supporter 308 wishes to know or learn additional information about a patient's medical condition. For example, the supporter 308 can want to be provided with additional context regarding the patient's medical condition, such as diabetes. As such, in certain aspects, the analyte monitoring application can share the patient's insulin data in addition to or as an alternative to the patient's glucose data with a supporter. The analyte monitoring application can also receive alerts from devices other than the patient's transmitter (e.g., insulin alerts, rather than high/low alerts).

The patient's insulin data (or other analyte data) can be shared via different pathways. One example pathway includes (i) the patient's insulin pump device or insulin pen sending data to the server system 330 and (ii) the server system 330 sending the data to the supporter device 311. Another example pathway includes (i) the patient's insulin pump device or insulin pen sending data to a server associated with the patient's insulin pump device or to a server associated with the patient's insulin pen and (ii) the server associated with the patient's insulin pump device or the server associated with the patient's insulin pen sending data to the supporter device 311.

Figure 5:
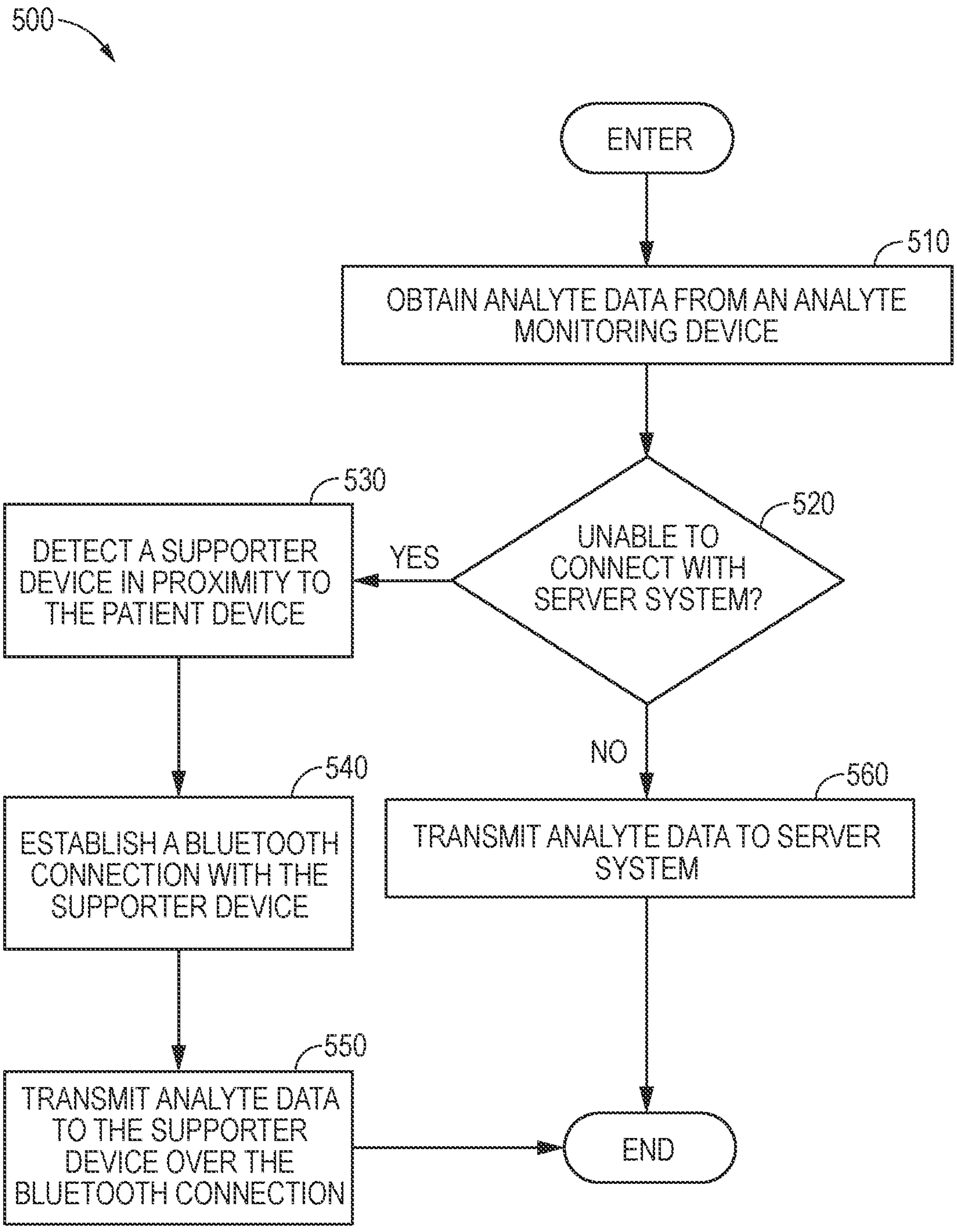
FIG. 5 is a flow diagram illustrating example operations for communicating analyte data, according to certain aspects described herein.

FIG. 5 is a flow diagram illustrating example operations 500 for communicating analyte data of a user (e.g., patient), according to certain aspects described herein. The operations 500 can be performed by a patient device (e.g., patient device 107).

At operation 510, the patient device obtains analyte data from an analyte monitoring device (e.g., analyte monitoring device 104). At operation 520, the patient device determines whether it is unable to connect with a server system (e.g., server system 330). As noted, the patient device can be unable to connect with the server system due to, e.g., losing internet connectivity, a server-side failure, etc.

If, at operation 520, the patient device is able to connect with the server system, then, at operation 560, the patient device transmits analyte data to the server system, e.g., using a WiFi or cellular communication. On the other hand, if, at operation 520, the patient device is unable to connect with the server system, then, at operation 530, the patient device detects a supporter device (e.g., supporter device 311) in proximity to the patient device. At operation 540, the patient device establishes a Bluetooth connection with the supporter device. Alternatively, as discussed above, at operation 540, the patient device implements a connection hierarchy and attempts to connect to the server system via a sequence of different connection types (e.g., WiFi, Bluetooth, NFC, etc.). At operation 550, the patient device transmits analyte data to the supporter device over the Bluetooth connection (or via another connection type included in the connection hierarchy).

In this manner, the patient device can implement operations 500 to connect with a supporter device and share the patient's analyte data when the patient device loses internet connectivity, which in turn can allow one or more other users to help the patient in certain emergencies, including, for example, hypoglycemic episodes, hyperglycemic episodes, etc.

Figure 6:
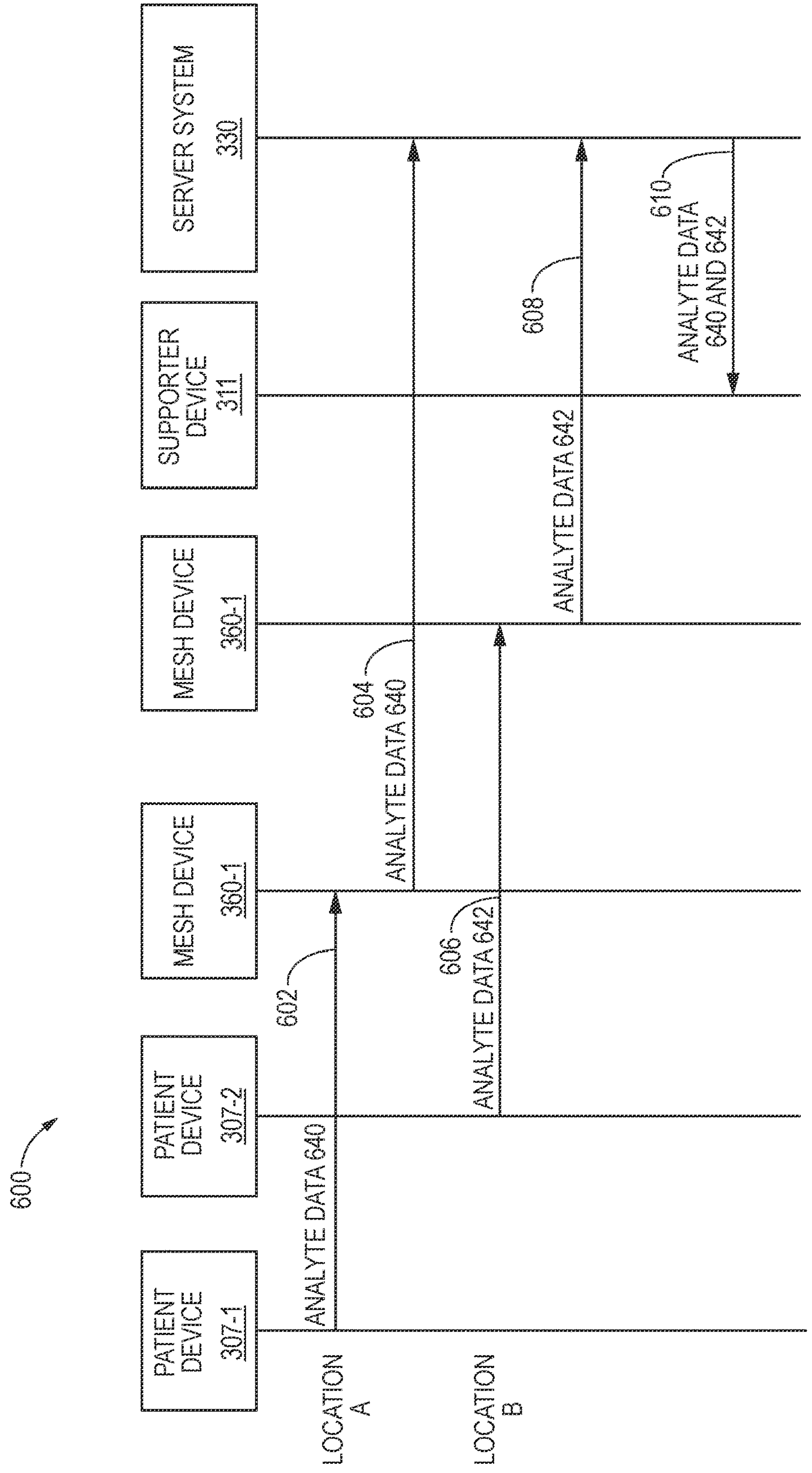
FIG. 6 is a sequence diagram illustrating example operations performed by one or more patient devices, one or more mesh devices, a supporter device, and a server system, according to certain aspects described herein.

FIG. 6 is a sequence diagram 600 illustrating example operations performed by one or more patient devices 107, one or more mesh devices 360, a supporter device 311, and a server system 330, according to certain aspects described herein.

As noted, in certain aspects, a hospital environment can deploy multiple mesh devices 360 (e.g., Bluetooth mesh devices) throughout the hospital in order to create a Bluetooth mesh for sharing multiple patients' analyte data. In such aspects, each patient device 307 (and/or analyte monitoring device 104) can be configured to send a respective patient's analyte data directly to a mesh device 360 in vicinity (or proximity) to that patient at a particular point in time. The mesh device(s) 360 can then transmit the patient's analyte data to a server system 130 in the hospital.

For example, at step 602, the patient device 307-1 for a first patient transmits the first patient's analyte data 640 to a mesh device 360-1 when the first patient is in location A (e.g., first patient's room in hospital). The patient device 307-1 can transmit the first patient's analyte data 640 to the mesh device 360-1 via Bluetooth. At step 604, the mesh device 360-1 forwards the first patient's analyte data 640 to the server system 330, e.g., via WiFi or cellular communications.

Similarly, at step 606, the patient device 307-2 for a second patient transmits the second patient's analyte data 642 to a mesh device 360-2 when the second patient is in location B (e.g., second patient's room in hospital). The patient device 307-2 can transmit the second patient's analyte data 642 to the computing device 360-2 via Bluetooth. At step 604, the mesh device 360-2 forwards the second patient's analyte data 642 to the server system 330, e.g., via WiFi or cellular communications.

At step 610, the server system 330 transmits the first patient's analyte data 640 and the second patient's analyte data 642 to a hospital supporter device 311. An exemplary server system 330 in a hospital environment can be accessed by authorized medical professionals responsible for taking care of multiple patients in the hospital. For example, in some aspects, a medical professional responsible for taking care of multiple patients with an analyte monitoring device 104 within the hospital is able to use a hospital supporter device 311 (e.g., smartphone, tablet, smart television, etc.) to view and monitor analyte data (e.g., glucose data, insulin data, etc.) being shared via Bluetooth from multiple patients in the hospital.

For instance, the hospital supporter device 311 can execute an analyte monitoring application that provides a dashboard for a large group of patients using a CGM monitoring device. In such an example, the glucose data of the patients can be shown using a view graph on the hospital supporter device 311. Additionally, in certain aspects, such an application can allow the medical professional to rearrange the analyte data of different patients according to various criteria/categories. For example, the analyte data 640, 642 can be shown according to highest glucose value, lowest glucose value, currently alerting, no data available, etc. Advantageously, adding mesh devices in this manner can enable a medical professional to more easily view and access multiple patients' data in an environment.

Although the sequence diagram 600 of FIG. 6 is described with respect to one or more mesh devices 360 implemented in a hospital environment, other environments are contemplated. For example, one or more mesh devices 360 can be implemented in a home setting, enabling the patient device 307 to transmit analyte data to at least one of the server system 330 or to the supporter device(s) 311 of one or more supporters 308 included in their family. Additionally or alternatively, one or more supporter device(s) 311 can operate as mesh device(s) 360 to form a mesh network (e.g., a Bluetooth mesh network) in a home setting, enabling the patient device 307 of one family member to transmit analyte data via the mesh network of the supporter device(s) 311 of their family members. Additionally or alternatively, a mesh network formed by the supporter device(s) 311 of family members can be implemented outside of a home setting, such as in one or more locations having poor cellular reception (e.g., large buildings, in the wilderness, etc.).

Certain aspects herein provide techniques for enhancing peer-to-peer sharing of analyte data. Certain environments, such as hospitals, can restrict the patient's ability to use their own analyte monitoring devices (i.e., CGM devices). For example, certain hospitals can require a patient to use a hospital provided CGM device (e.g., analyte monitoring device 104) that is configured to share patient glucose data with hospital server(s). In such an example, when a new patient that does not have a hospital provided CGM device enters the hospital, the new patient is unable to share the patient's glucose information using the patient's display device. Accordingly, in certain aspects, the patient device is configured to relinquish at least some of its management to the hospital when the patient initially enters the hospital.

Figure 7:
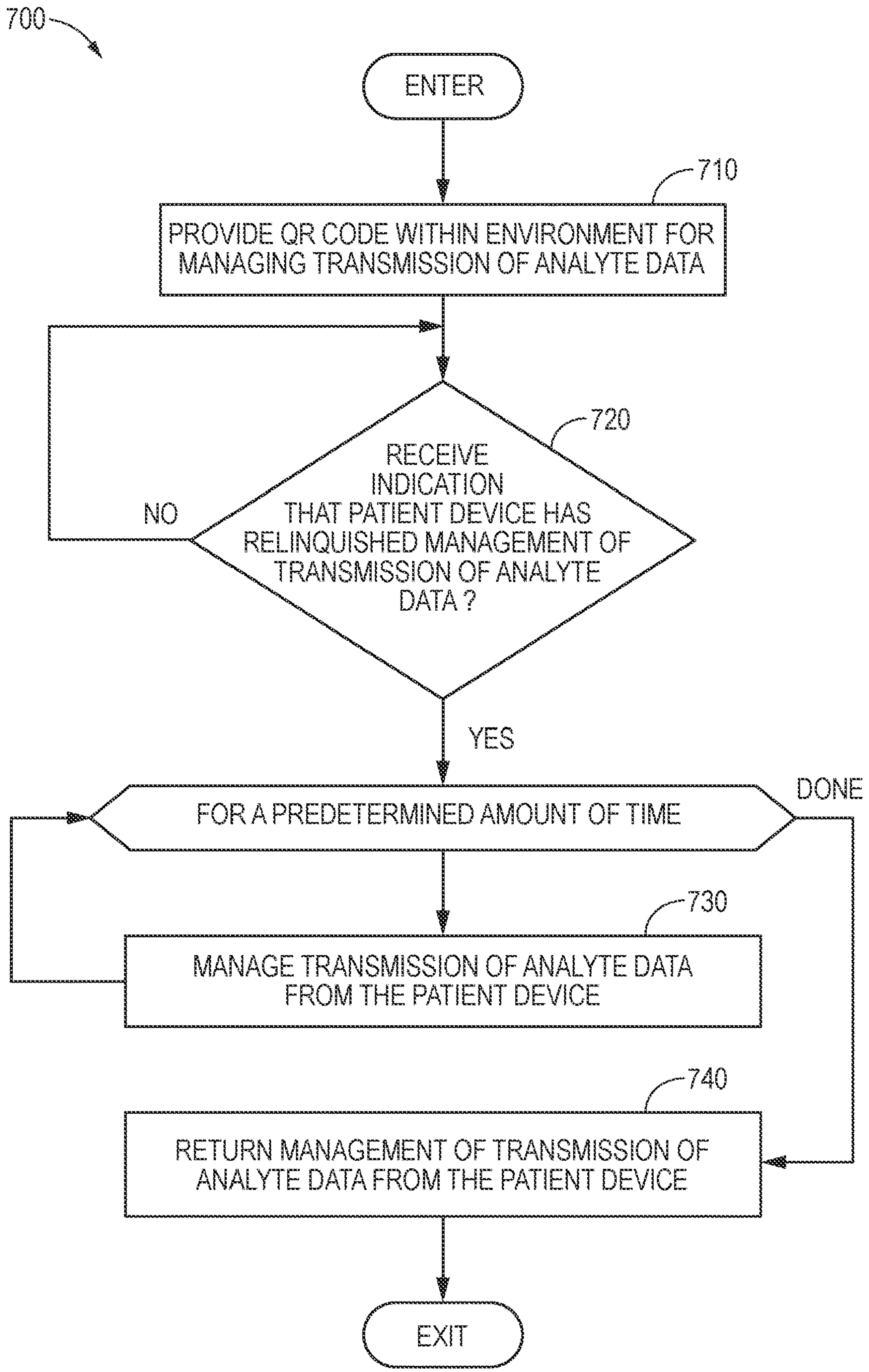
FIG. 7 is a flow diagram illustrating example operations for communicating analyte data, according to certain aspects described herein.

FIG. 7 is a flow diagram illustrating example operations 700 for communicating analyte data of a user (e.g., patient), according to certain aspects described herein.

At operation 710, a QR code is provided within the environment (e.g., hospital) for managing transmission of analyte data. For example, the hospital can provide a QR code that can be scanned by the patient device when the patient initially enters the hospital. When scanned by the patient, the QR code can automatically relinquish management of transmission of the patient's analyte data from the patient device to the server system 330.

At operation 720, the server system 330 determines whether an indication that the patient device has relinquished management of transmission of analyte data has been received (e.g., from the patient device 307). If the indication has not been received, the method remains at operation 720 until the server system 130 receives the indication. On the other hand, if the indication has been received, at operation 730, the server system manages transmission of analyte data from the patient device for a predetermined amount of time (e.g., 2 days or some other amount of time). In certain aspects, managing the transmission of analyte data can include at least one of (i) receiving the patient's analyte data from the patient device, (ii) monitoring the patient's analyte data, or (iii) transmitting alerts to the patient device based on the patient's analyte data.

In certain aspects, the hospital can also deploy a mesh of Bluetooth devices (e.g., mesh devices 360) within the hospital to facilitate peer-to-peer sharing in the hospital. In some cases, one or more of the Bluetooth devices (e.g., server, access point, etc.) can run an algorithm that is configured to find a person of interest, such as a doctor or another medical professional with the right skill set to address the patient's issue. In such an example, a patient's analyte data can be sent through multiple BLE devices until it reaches the determined person of interest.

In certain aspects, the configuration of the analyte monitoring application (running on the supporter device 311) can automatically adapt based in part on at least one of the geographical jurisdiction in which the supporter 308 is located or the supporter's 308 preferences. In some instances, for example, the supporter 308 prefers to see notifications in the supporter's native language. Additionally, in some cases, at least one of the error codes or unit(s) of measure used by the analyte monitoring application can change as the supporter 308 moves to different geographical jurisdictions. Similarly, the alerts for the patient's analyte data can be different in various geographical jurisdictions, due to regulatory reasons. In an exemplary scenario, a supporter device 311 located in Germany can still display information associated with the patient in English, based on that supporter's preferences.

As discussed above, the current invitation processes used to allow a patient to share their analyte data with a supporter 308 can be cumbersome and time consuming. For example, currently, in order to share analyte data with a supporter 308, the patient has to input the supporter's information (e.g., biographical information) into the analyte monitoring application (e.g., application 306-1) on the patient device 107, and generate an invitation to send to the supporter 308 to download an analyte monitoring application (e.g., application 306-2) on the supporter device 311. However, performing invitation in this manner is technically disadvantageous because it requires more compute and memory resources.

As such, certain aspects provide a simpler and technically more advantageous (e.g., more resource efficient) process for enabling a patient to share their analyte data with a user. In certain aspects, as opposed to using an invitation process, the patient's display device can send, to a supporter, an email with a link that allows the supporter to immediately access the patient's analyte data, e.g., without downloading an application, registering the supporter device, etc. Additionally alternatively, the patient's display device can display a QR code that can be scanned by a supporter device 311 to allow the supporter 308 to immediately access the patient's analyte data. In certain aspects, the patient's display device can communicate with a supporter device 311 via NFC communication to transmit the patient's analyte data. In any of the aspects described above, the analyte data shared with the supporter device 311 can have an associated expiration time and/or date after which the supporter device can no longer access the analyte data, and/or can have geographical or contextual limitations that, for example, enable the analyte data to be viewed only when the patient and the supporter 308 are a within a threshold distance from each other or when at least one of the patient or the supporter 308 are within predefined, geo-fenced area. In certain aspects, analyte data can be shared via a URL that is publicly accessible or which is accessible by authorized subscribers, such as based on inputting credentials (e.g., username and password) or based on an access list. In some aspects, the URL can link to a shared, community data folder that can be accessed by the patient and one or more supporters 308.

In certain aspects, when a patient shares data (e.g., analyte data, insulin data, etc.) with a supporter device 311 of a supporter 308 that is located in a different geographical jurisdiction, the server system can automatically process the data transmission request in a manner that adheres to regulatory guidelines, security protocols, and privacy laws. For example, if a supporter 308 located in a first geographical jurisdiction (e.g., Country A) receives an invite to view data from a patient in a second geographical jurisdiction (e.g., Country B), then a determination can be made as to whether the second geographical jurisdiction has a conflict that prevents the patient's data from being shared with a supporter 308 in the first geographical jurisdiction without appropriate permissions. If such a conflict exists, then a determination is made as to whether the invitation from the patient for the supporter to view the patient's data constitutes sufficient authorization within the second geographical jurisdiction. If the invitation constitutes sufficient authorization within the second geographical jurisdiction, then the data is sent from the second geographical jurisdiction to the supporter device 311 of the supporter 308 located in the first geographical jurisdiction (e.g., from a server system located in the second geographical jurisdiction to the supporter device 311 located in the first geographical jurisdiction). If, on the other hand, the invitation does not constitute sufficient authorization within the second geographical jurisdiction, then, in order to comply with the relevant regulations, the data is instead sent (i) from the second geographical jurisdiction (e.g., from a server system located in the second geographical jurisdiction) to a server system located in the first geographical jurisdiction, and then (ii) from the server system located in the first geographical jurisdiction to the supporter device 311 of the supporter 308 located in the first geographical jurisdiction.

Additionally or alternatively, in certain aspects, data being transmitted to a supporter device 311 across geographical jurisdictions can be repackaged (e.g., by a server system located in the second geographical jurisdiction) in order to remove one or more data types that cannot be transmitted from the second geographical jurisdiction to the first geographical jurisdiction. For example, the patient's data can be repackaged to remove data to which the supporter 308 does not have permissions or rights to view and/or data that is not allowed to be transmitted between the geographical jurisdictions. The repackaged data is then transmitted to the supporter device 311 located in the first geographical jurisdiction either (i) directly to the supporter device 311 from a server system located in the second geographical jurisdiction or (ii) from a server system located in the second geographical jurisdiction to the supporter device 311 via a server system located in the first geographical jurisdiction.

Additionally, certain aspects can allow certain supporters to restrict patients from modifying the supporter's permissions associated with the sharing of the patient's analyte data. For example, if a supporter is a parent and the patient is a child, then in certain aspects, the child's analyte monitoring application can restrict the ability of the child to modify permission(s) for the parent.

Additionally, in some cases, at least one of a patient or supporter may wishes to untether from a specific device (e.g., smartphone) for receiving notification/alerts. In such cases, an alternate device can be configured to relay notification/alerts to the patient, to the supporter, or to both the patient and the supporter. An exemplary alternate device can include a non-battery powered device (e.g., wall plug in device, such as smart speaker), which the patient and/or supporter does not have to carry around.

As discussed, certain aspects provide a set of features that create a stronger connection and additional support between the supporter 308 and the patient. For example, the analyte monitoring application can allow a supporter to interact in various ways that support a particular patient.

Figure 8A:
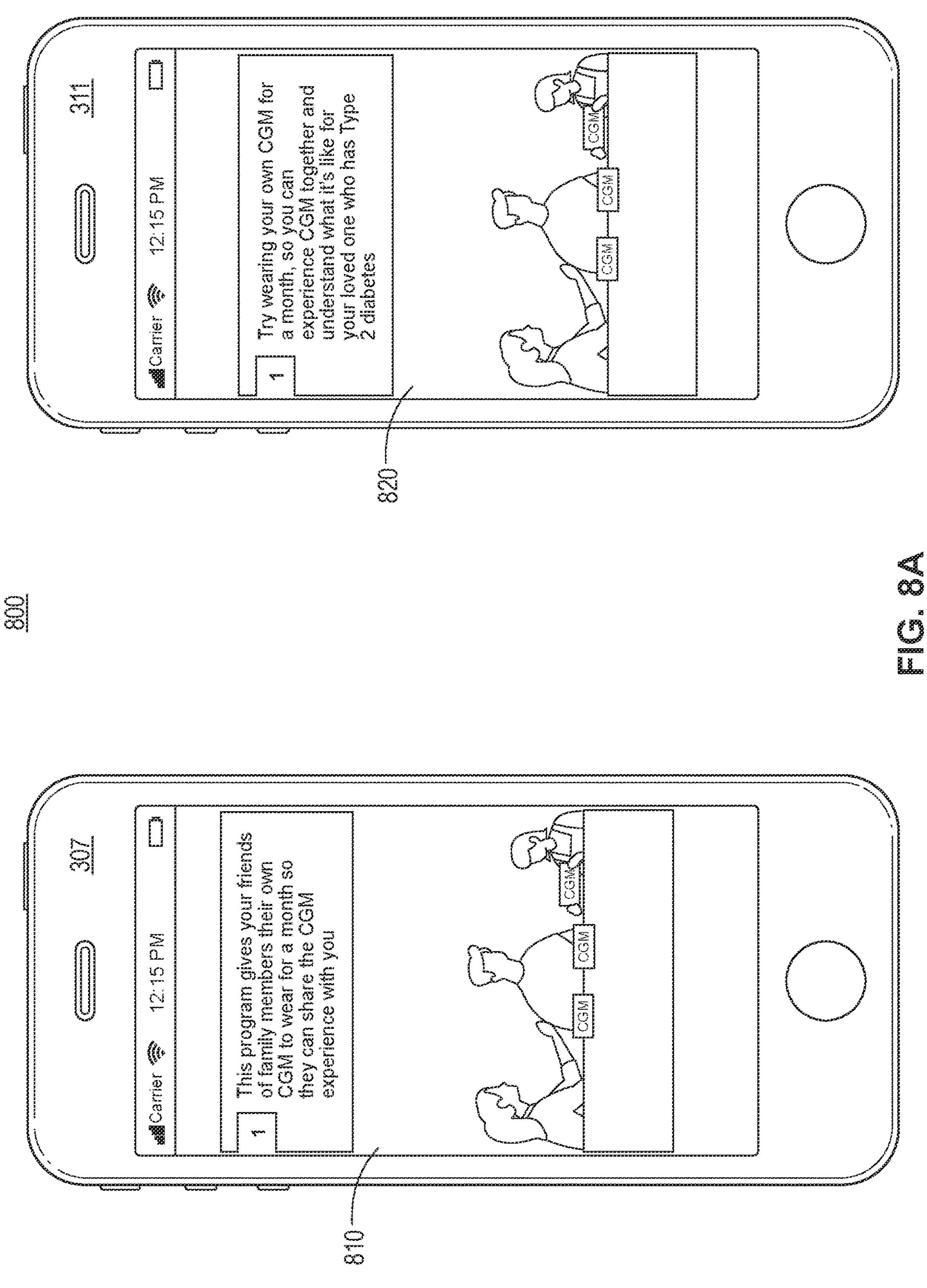
FIGS. 8A-8C illustrate an example scenario for providing social support to a patient, according to certain aspects described herein.
Figure 8B:
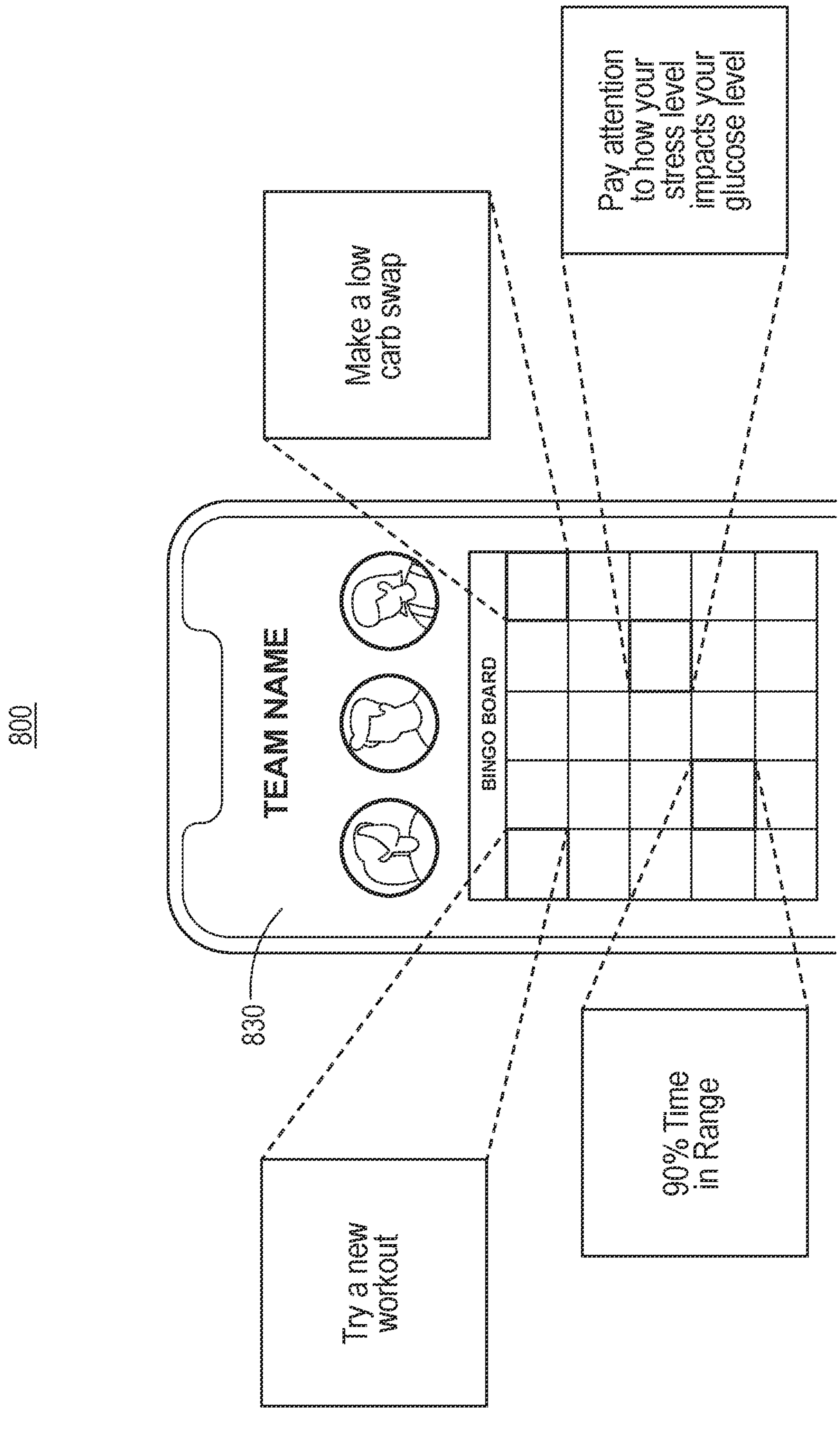
Figure 8C:
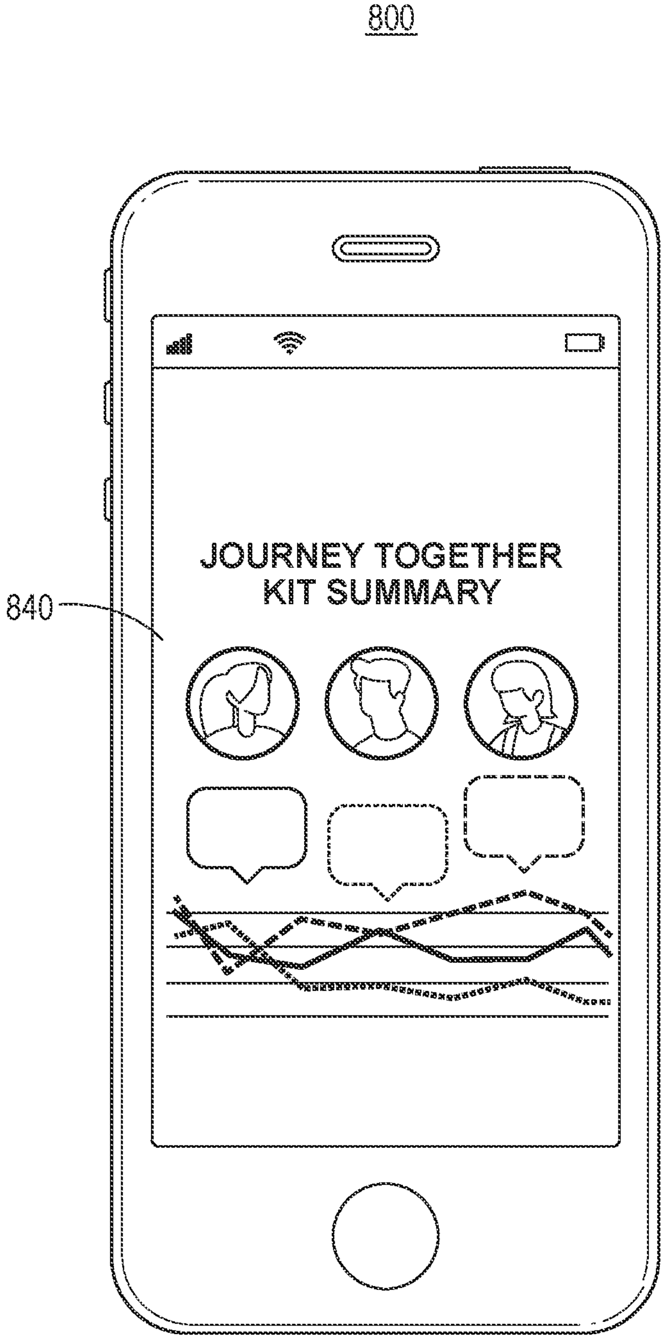

FIGS. 8A-8C illustrate an example scenario 800 for providing social support to a patient, according to certain aspects described herein. In particular, FIGS. 8A-8C depict example UIs that can be provided by an analyte monitoring application for display on a patient device 307 and a supporter device 311.

In the scenario 800, the analyte monitoring application allows a group of users (e.g., family or group of friends) to start a health monitoring trial together as part of a "journey together" program. The health monitoring trial can last for a predetermined amount of time (e.g., 1 month, 3 months, etc.). For example, the health monitoring trial gives a user included in a group of users (e.g., patient and the patient's supporters) their own analyte monitoring device 104 (e.g., CGM device or sensor) to wear for a period of time so that each supporter in the group can share the health monitoring experience with the patient. An exemplary "journey together kit," can include a set of analyte monitoring devices 104 (e.g., a respective CGM sensor for each person the group). Each supporter 308 can scan the barcode on a respective analyte monitoring device 104 with a supporter device 311 (e.g., mobile phone). Once scanned, the respective supporter device 311 can pull information from each other supporter's analyte monitoring device from a cloud server (e.g., server system 330) and display each supporter's analyte stream in one trend graph, which displays each supporter's glucose trend alongside the patient.

In FIG. 8A, the UI 810 displays an introduction to the "journey together" program on the patient device 307 and the UI 820 displays an introduction to the "journey together" program on the supporter device 311. As part of the "journey together" program, the patient is able to share/start the patient's analyte monitoring journey together with other supporters 308.

The analyte monitoring application can allow the patient to participate in games and challenges with other supporters as part of the "journey together" program in order to motivate the patient to achieve the patient's health goals and/or to make the patient feel supported by having their supporters participate in the same experience. In FIG. 8B, for example, the UI 830 displays a game used as part of the "journey together" program. The UI 830 can be presented on the patient device 307 and the supporter device 311. Here, the game is displayed on a bingo board, which includes analyte-related behavior boxes. The patient can perform the various analyte-related behaviors (e.g., trying a new workout, being within an analyte range for a particular percentage of a day, or swapping to a low carb diet) in order to "fill-in" related squares on the bingo board.

The analyte monitoring application can also allow the patient to compare the patient's analyte data (e.g., glucose data) with other supporters as part of the "journey together" program. The analyte monitoring application can provide a summary report highlighting how the patient's data compares with other users' data. Such a summary report can provide educational insights regarding the user's condition (e.g., Type 2 diabetes) in order to help the group better understand the user's health management. In FIG. 8C, for example, the UI 840 displays analyte data (e.g., analyte traces) for all users in the group and/or one or more educational insights for those users based on determined trends. The UI 840 can be presented on the patient device 307 and the supporter device 311.

In an exemplary scenario, imagine that a family starts a one-month program to go on a health monitoring journey together. As they are going through the experience of wearing an analyte monitoring sensor, they will have opportunities to journal and understand the impact of different events going on with their analyte levels. As such, the "journey together kit" provides an opportunity for family members to connect and understand how the analyte monitoring sensor is impacting their health, as well as their family members' health. As an example, the family can eat the same food for dinner together and monitor, via the analyte monitoring application, the effect the dinner has on each person's analyte measurements. In such an example, the family is able to identify that a certain meal has a particular effect on the patient's analyte measurements but does not have that particular effect on other family members. The family can further identify that a certain meal has a negative or positive impact across the entire group.

FIGS. 9A-9D illustrate an example scenario 900 for providing social support to a patient, according to certain aspects described herein. In particular, FIGS. 9A-9D depict example UIs that can be provided by an analyte monitoring application for display on a patient device 307, a supporter device 311, or a patient device 307 and a supporter device 311.

In scenario 900, the analyte monitoring application allows a patient to receive recognition from one or more supporters 308, based on the patient's shared analyte data. The patient can select to permit one or more supporters 308 to follow the patient's analyte data, and the permitted supporters can be sent or displayed daily highlights with explanations of what went well that day for the patient. The one or more supporters 308 can also receive real-time notifications when the patient is experiencing a good (or less optimized) analyte moment. The analyte monitoring application also allows the supporter(s) to send messages (e.g., acknowledgments or encouragement) alongside a particular analyte moment to the patient to encourage and motivate the patient, based on the patient's analyte data. Additionally, the analyte monitoring application also allows the supporter(s) to send messages that can be acknowledged by the patient, such as messages requesting an acknowledgement that certain actions have been taken by the patient (e.g., a medication has been taken, a particular dose of insulin has been administered, a meal has been consumed, etc.).

Figure 9A:
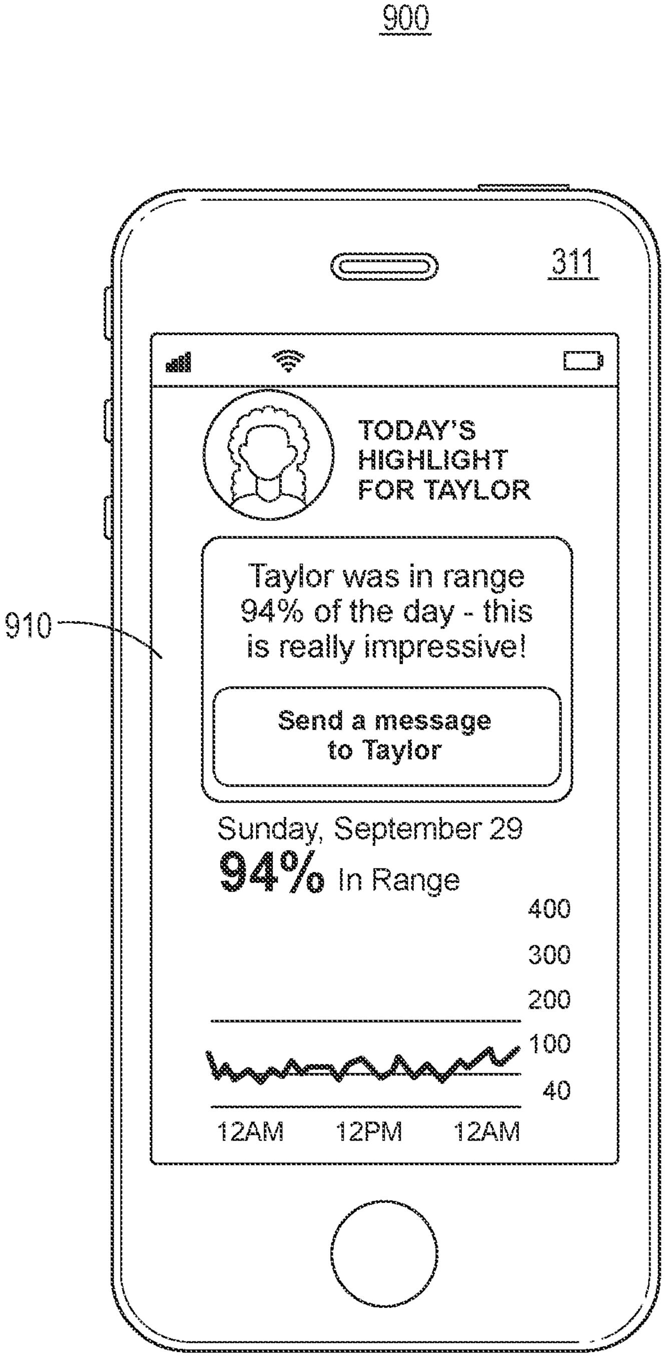
FIGS. 9A-9E illustrate another example scenario for providing social support to a patient, according to certain aspects described herein.
Figure 9B:
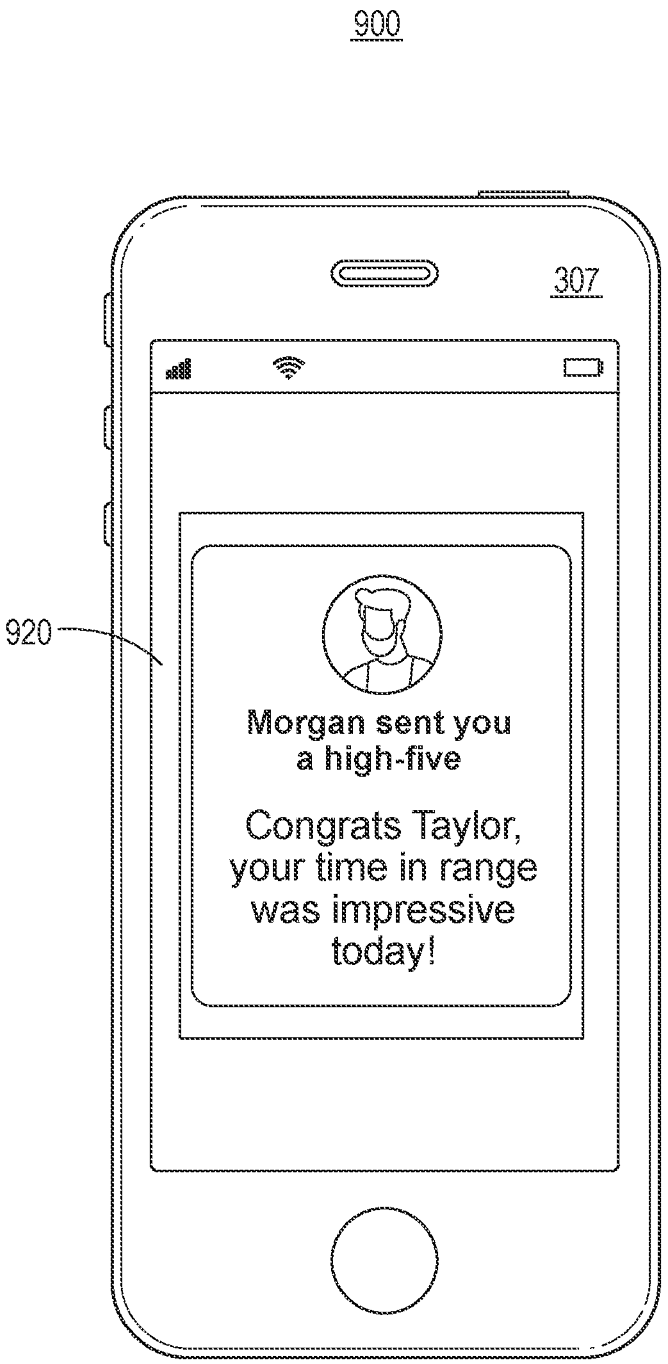

In certain aspects, the analyte monitoring application provides current information on the patient's health trends. For example, the analyte monitoring application can provide current information on the patient's analyte trend for a given date. Providing such information to the supporter 308 enables the supporter 308 to view the patient's analyte highlights and send messages (e.g., acknowledgements) when the patient meets a health goal. For example, the analyte monitoring application can highlight key moments of progress for the patient and prompt the supporter 308 to send a message to the patient. In FIG. 9A, for example, the UI 910 displays the patient's analyte data (e.g., glucose data), analyte highlights, or patient's analyte data and analyte highlights on the supporter device 311, so that the supporter 308 can see what went well for the patient. The UI 910 also displays graphical elements with which a supporter 308 can interact to send the patient a message to show support, e.g., when the patient meets a health goal. In FIG. 9B, the UI 920 displays an exemplary message from a supporter 308 that has been received by the patient via the patient device 307.

In addition to or as an alternative to sending messages, such as acknowledgments, in certain aspects, the analyte monitoring application can identify moments in which the patient has not reached a health goal and can prompt the supporter 308 to send a message to the patient to motivate the patient to reach their health goal and/or change a behavior of the patient. For example, if the patient has had an analyte spike after lunch time for the past several days, the analyte monitoring application can prompt the supporter 308 to send a message to the patient suggesting that the patient choose a different lunch option.

Figure 9C:
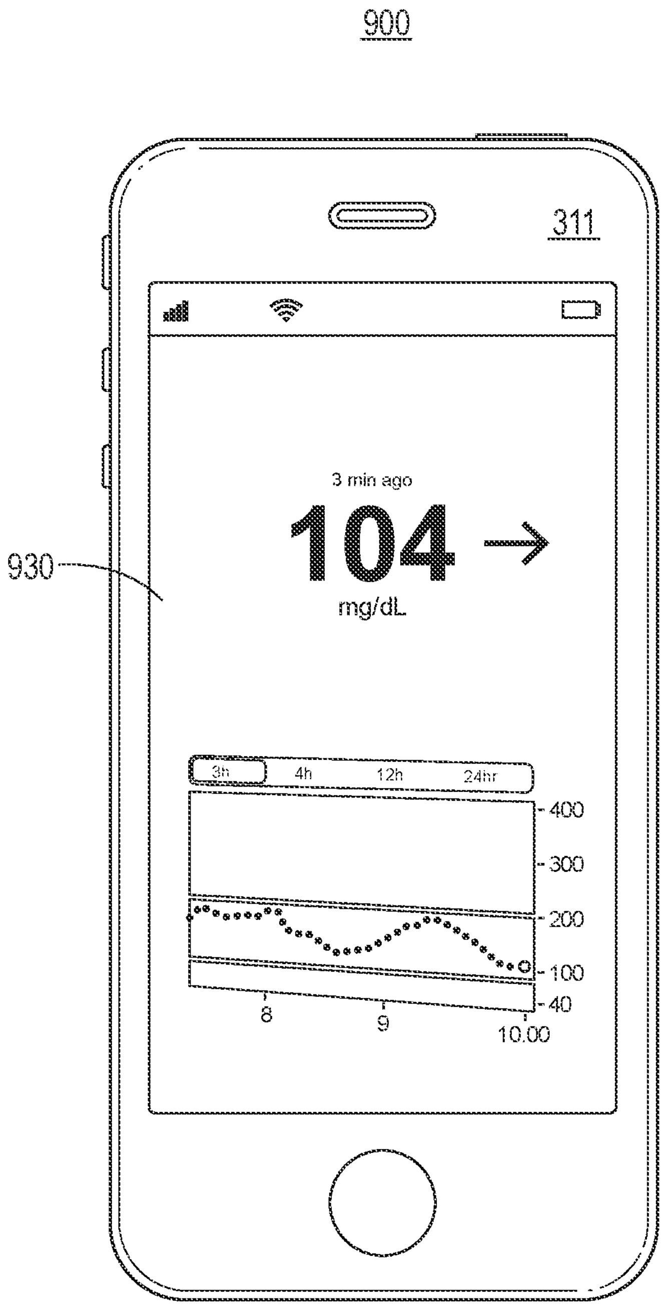
Figure 9D:
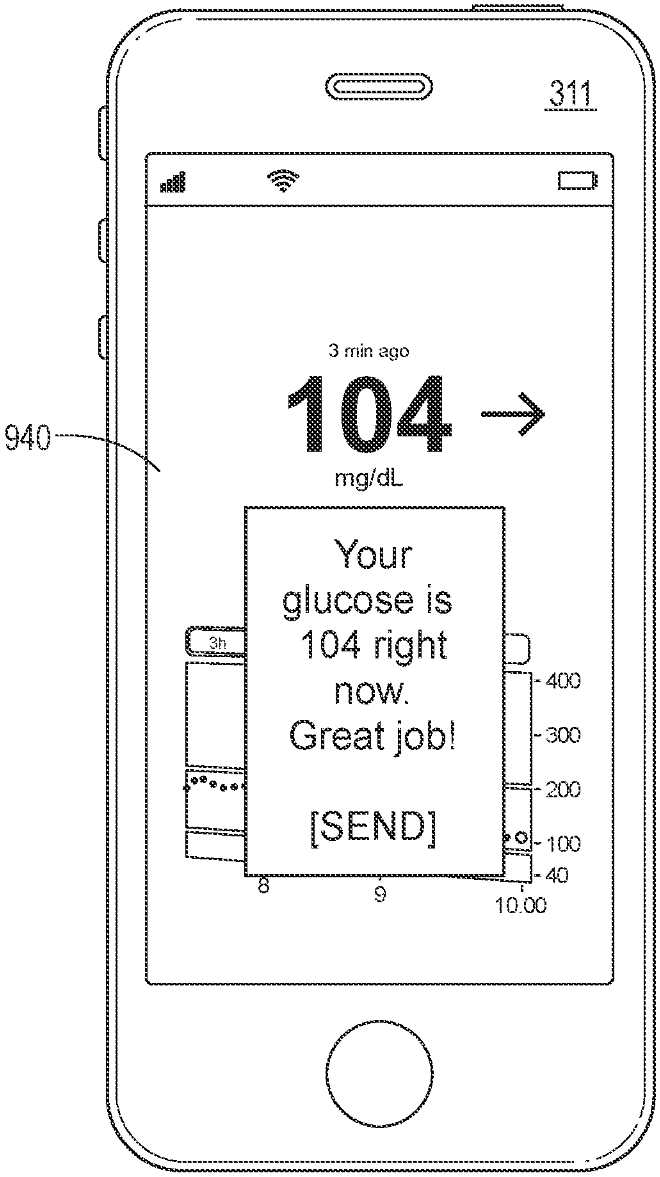
Figure 9E:
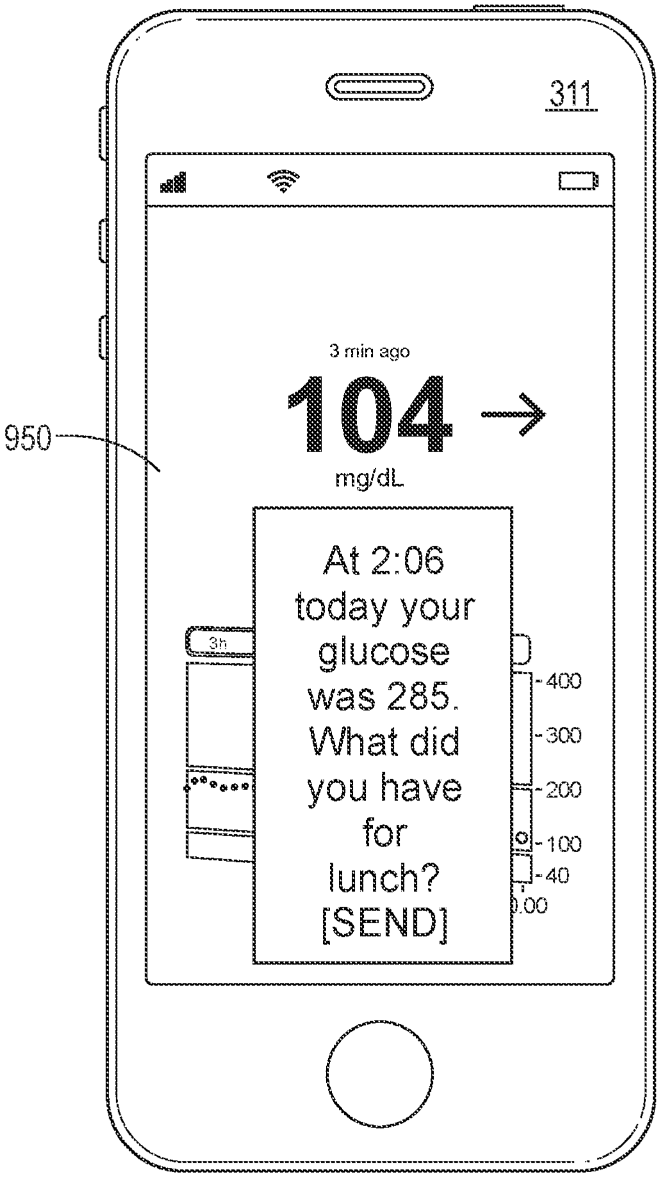

In certain aspects, the analyte monitoring application can display a trend graph containing the patient's analyte data on the supporter device 311. FIG. 9C illustrates an example UI 930, which displays a trend graph for a patient on the supporter device 311. In such an aspect, the analyte monitoring application can allow the supporter 308 to tap on a current analyte value or on a point or time range in the trend graph to create an "analyte highlight" to send to the patient. Such an "analyte highlight" can state the time and the analyte value, and can include a message. For example, when the supporter 308 taps/selects the current glucose value "104" in the UI 930, the UI 940 in FIG. 9D displays an "analyte highlight" with the following message "Your glucose is 104 right now. Greatjob!" on the supporter device 311. In another example, when the supporter 308 taps/selects a point in the trend graph in the UI 930, the UI 950 in FIG. 9E displays an "analyte highlight" with the following message "At 2:06 pm today, your glucose was 285. What did you have for lunch?" on the supporter device 311. In yet another example, when the supporter 308 taps/selects a time range in the trend graph in the UI 930, the UI 950 in FIG. 9E displays an "analyte highlight" with the following message "Your glucose spiked between 12:05 pm and 2:45 pm today. What did you have for lunch?" on the supporter device 311. Note, in general, the message can be selected from a set of predefined messages or can be a custom message. Once the supporter 308 selects to send the "analyte highlight," the analyte monitoring application can display the "analyte highlight" alongside the message on the patient device 307. Such aspects enable a supporter 308 to provide feedback, such as encouragement or coaching, to the patient based on their analyte data. For example, a supporter 308 (e.g., a coach) can tap on an analyte value or on a point or time range in a trend graph and associate one or more messages with the analyte value or trend graph indicating a type of exercise that was performed during the corresponding time period, or a type of food or beverage that was consumed during the corresponding time period.

In certain aspects, the analyte monitoring application allows a patient, a supporter 308, or a patient and a supporter 308 to access a portal that includes educational resources regarding the patient's health condition, discussion points for facilitating conversations between the patient and the supporters, challenges/games/activities that the supporters and patients can complete in order to motivate the patient in meeting health goals, and the like. In such an aspect, the analyte monitoring application can provide the supporter with education (e.g., information resources) on the patient's medical condition (e.g., diabetes), suggestions for talking points for facilitating discussions between the supporter and patient, recommendations for actions that the supporter can take to help the patient with their health condition, etc. For example, in certain aspects, the analyte monitoring application can generate personalized recommendations of discussion points and actions to take for each member of a group including one or more supporters 308 and the patient. Additionally or alternatively, the analyte monitoring application allows a patient to specify one or more types of support that are preferred by the patient and which, for example, are most likely to encourage the patient to reach their goal(s). In certain aspects, the analyte monitoring application also allows a patient to permit, throttle, or eliminate one or more types of support that they receive from supporter(s) 311, for example, by eliminating types of feedback that are not effective in encouraging the patient to reach their goal(s). In various aspects, the type(s), frequency, or type(s) and frequency of support requested from supporters 311 (or permitted to be submitted by supporters 311) can be determined based on a patient's explicit preferences, as discussed above, or can be automatically determined based on a patient's age, based on historical data indicating one or more types of feedback that are effective in controlling a patient's analyte levels, or based on a determination of the features of the analyte monitoring application with which the patient most often interacts (e.g., stickers, badges, analytes highlights, text messages).

Figure 10:
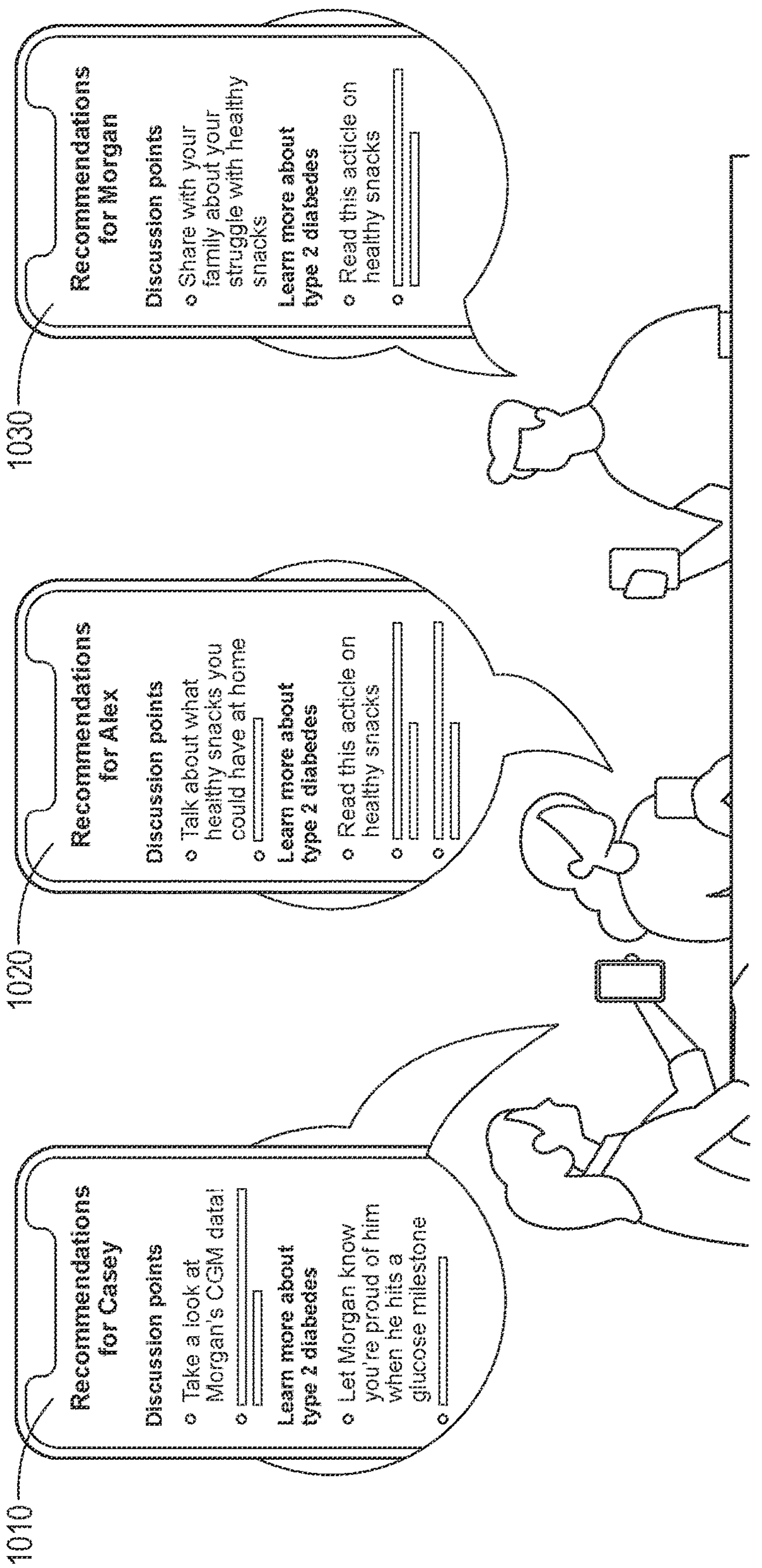
FIG. 10 illustrates another example scenario for providing social support to a patient, according to certain aspects described herein.

FIG. 10, for example, depicts example UIs that can be provided by an analyte monitoring application for display on a patient device 307, a supporter device 311, or a patient device 307 and a supporter device 311. Here, UI 1010 displays set of personalized discussion points for a first supporter 308 regarding the patient's health management, UI 1020 displays a set of personalized discussion points for a second supporter 308 regarding the patient's health management, and UI 1030 displays a set of personalized discussion points for a third supporter 308 regarding the patient's health management.

Additionally, in certain aspects, the analyte monitoring application on a patient's display device can generate, for each supporter 308 of the patient, personalized recommendations of discussion points and actions to take for the supporter 308. The patient can then show each supporter 308 the set of personalized recommendations and actions to show the supporter 308 how they can most effectively interact with the patient and facilitate conversations around the patient's health condition.

Certain aspects can provide a supporter assessment tool that is configured to assess different types of support, and determine which ones work best for the particular patient. For example, supporters oftentimes do not really know how best to support the patient that they are supporting. As such, in certain aspects, the supporter assessment tool can evaluate a variety of different support tools to determine which ones work best based on the profile of a particular patient. The supporter assessment tool can then provide an indication of the best support tools to the supporter. Note, the supporter assessment tool can evaluate the different support tools using a variety of techniques, including, for example, rule-based techniques, artificial intelligence/machine learning techniques, etc.

The supporter assessment tool can also evaluate the effectiveness of the recommended support tools being used by supporters for a particular patient to determine whether to update the recommended support tools.

More details regarding providing support to a patient using an analyte monitoring application can be found in U.S. Provisional Application No. 63/289,376, filed Dec. 14, 2021, which is incorporated herein by reference in its entirety for all purposes.

Figure 11:
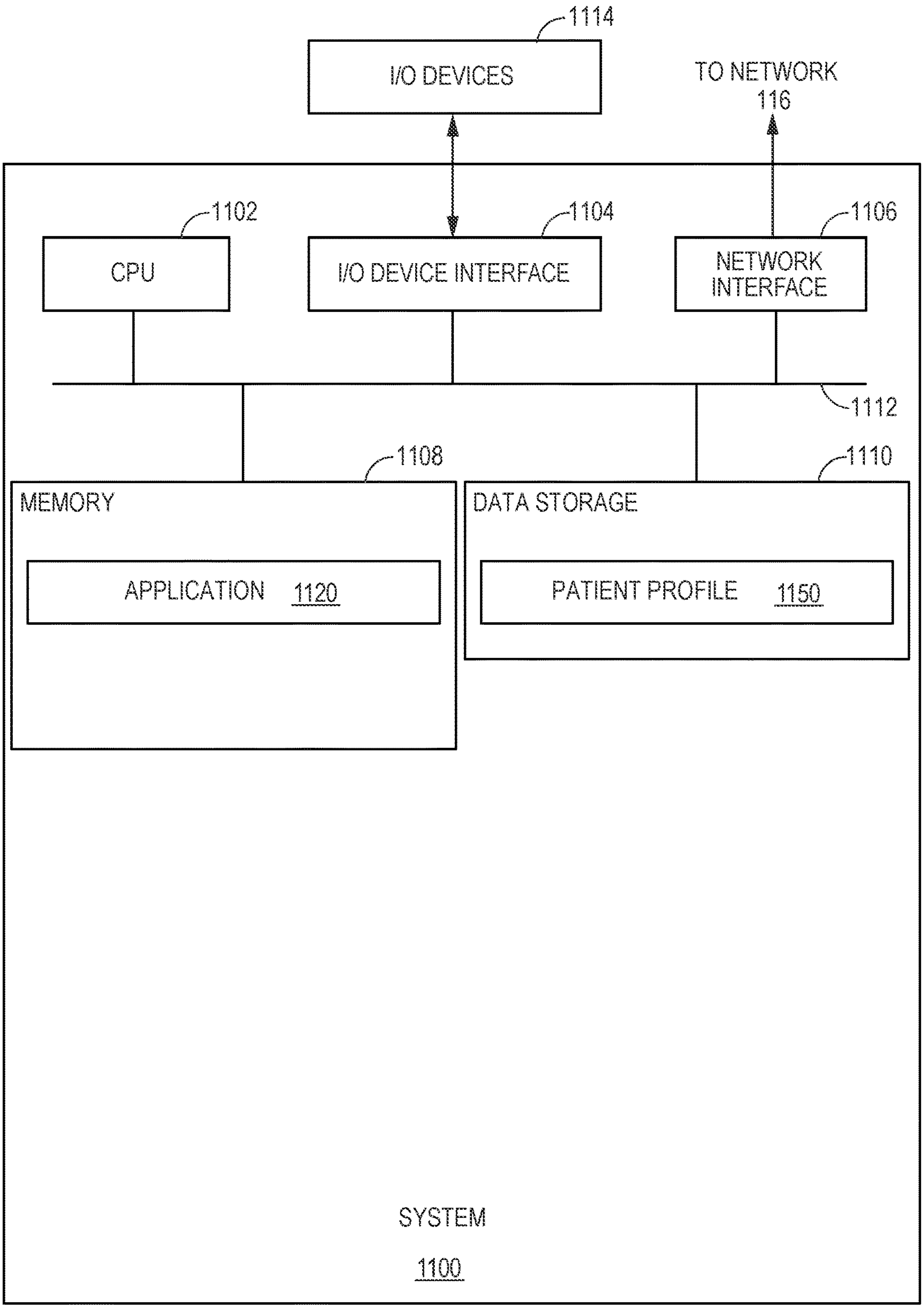
FIG. 11 is a diagram of an aspect of a processing system that performs or embodies certain aspects described herein.

FIG. 11 is a diagram of an aspect of a processing system that performs or embodies certain aspects described herein.

For example, in some aspects, system 1100 corresponds to the patient device 307 or the supporter device 311 illustrated in FIG. 3.

As shown, system 1100 includes a central processing unit (CPU) 1102, one or more I/O device interfaces 1104 that can allow for the connection of various I/O devices 1114 (e.g., keyboards, displays, mouse devices, pen input, etc.) to the system 1100, network interface 1106 through which system 1100 is connected to the network 116, a memory 1108, a data store 1110, and an interconnect 1112.

The CPU 1102 can retrieve and execute programming instructions stored in the memory 1108. Similarly, the CPU 1102 can retrieve and store application data residing in the memory 1108 or accessible via the network 116. The interconnect 1112 transmits programming instructions, interactions, and application data, among the CPU 1102, I/O device interface 1104, network interface 1106, and memory 1108. The memory 1108 is representative of a volatile memory, such as a random access memory; a nonvolatile memory, such as nonvolatile random access memory, phase change random access memory; a volatile memory and a nonvolatile memory; or the like. As shown, memory 1108 includes application 1120 (e.g., analyte monitoring application, such as application 306), which, when executed by the CPU 1102 performs the operation described herein with respect to application 306. The data storage 1110 can store various data, such as analyte data 120 stored locally, personalized thresholds, and the like.

Example Aspects

Aspect 1: A computer-implemented method performed by a first display device for communicating analyte data, the computer-implemented method comprising: obtaining analyte data from an analyte monitoring device; detecting that the first display device has lost connectivity with a server computing system; and in response to detecting that the first display device has lost connectivity with the server computing system: automatically initiating a scan for one or more display devices; upon detecting, based on the scan, a second display device of the one or more display devices that is in proximity to the first display device, establishing a communication link with the second display device; and transmitting the analyte data to the second display device.

Aspect 2: The computer-implemented method of Aspect 1, wherein detecting that the first display device has lost connectivity with the server computing system comprises determining that a predefined amount of time has elapsed since receiving a message from the server computing system.

Aspect 3: The computer-implemented method of Aspects 1 or 2, wherein detecting that the first display device has lost connectivity with the server computing system comprises determining that the first display device has lost at least one of WiFi connectivity or cellular connectivity with the server computing system.

Aspect 4: The computer-implemented method of any of Aspects 1-3, wherein the communication link is a Bluetooth communication link.

Aspect 5: The computer-implemented method of any of Aspects 1-4, wherein the one or more display devices are indicated on a whitelist associated with the first display device.

Aspect 6: The computer-implemented method of any of Aspects 1-5, further comprising presenting a list of the one or more display devices on a user interface of the first display device.

Aspect 7: The computer-implemented method of any of Aspects 1-6, wherein the one or more display devices are not associated with a whitelist associated with the first display device.

Aspect 8: The computer-implemented method of any of Aspects 1-7, further comprising receiving an indication of the second display device that has been selected from the list of the one or more display devices presented on the user interface of the first display device.

Aspect 9: A computer-implemented method comprising: receiving an indication that a display device associated with a user has relinquished management of transmission of analyte data from the display device; and in response to receiving the indication, managing transmission of analyte data from the display device for a predetermined amount of time.

Aspect 10: The computer-implemented method of Aspect 9, further comprising returning management of the transmission of analyte data from the display device to the display device after the predetermined amount of time has elapsed.

Aspect 11: The computer-implemented method of Aspects 9 or 10, wherein the indication comprises a message indicating that the user has scanned a quick response (QR) code within an environment.

Aspect 12: The computer-implemented method of any of Aspects 9-11, wherein managing transmission of analyte data comprises triggering the display device to transmit analyte data upon occurrence of a predetermined condition.

Aspect 13: The computer-implemented method of any of Aspects 9-12, further comprising, after receiving the analyte data from the display device, forwarding the analyte data to another display device.

Aspect 14: The computer-implemented method of any of Aspects 9-13, further comprising, after receiving the analyte data from the display device, transmitting at least one message to the display device based on an analysis of the analyte data.

Aspect 15: A first display device comprising: at least one processor; and a memory storing executable instructions, which when executed by the at least one processor, perform an operation comprising: obtaining analyte data from an analyte monitoring device; detecting that the first display device has lost connectivity with a server computing system; and in response to detecting that the first display device has lost connectivity with the server computing system: automatically initiating a scan for one or more display devices; upon detecting, based on the scan, a second display device of the one or more display devices that is in proximity to the first display device, establishing a communication link with the second display device; and transmitting the analyte data to the second display device.

Aspect 16: The first display device of Aspect 15, wherein detecting that the first display device has lost connectivity with the server computing system comprises determining that a predefined amount of time has elapsed since receiving a message from the server computing system.

Aspect 17: The first display device of Aspects 15 or 16, wherein detecting that the first display device has lost connectivity with the server computing system comprises determining that the first display device has lost at least one of WiFi connectivity or cellular connectivity with the server computing system.

Aspect 18: The first display device of any of Aspects 15-17, wherein the one or more display devices are indicated on a whitelist associated with the first display device.

Aspect 19: The first display device of any of Aspects 15-18, further comprising presenting a list of the one or more display devices on a user interface of the first display device.

Aspect 20: The first display device of any of Aspects 15-19, further comprising receiving an indication of the second display device that has been selected from the list of the one or more display devices presented on the user interface of the first display device.

Each of these non-limiting examples can stand on its own or can be combined in various permutations or combinations with one or more of the other examples. The above detailed description includes references to the accompanying drawings, which form a part of the detailed description. The drawings show, by way of illustration, specific aspects in which the invention can be practiced. These aspects are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other aspects can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter may lie in less than all features of a particular disclosed aspect. Thus, the following claims are hereby incorporated into the Detailed Description as examples or aspects, with each claim standing on its own as a separate aspect, and it is contemplated that such aspects can be combined with each other in various combinations or permutations. The scope of the invention should be determined with reference to the appended claims, along with the full scope of equivalents to which such claims are entitled.

What is claimed is:

1. A computer-implemented method performed by a first display device for communicating analyte data, the computer-implemented method comprising:

obtaining, by the first display device, analyte data from an analyte monitoring device;

determining, by the first display device, that one or more values of the analyte data exceed a first threshold or drop below a second threshold;

attempting, by the first display device, to share the analyte data with a second display device separate from the first display device via a server computing system, where the server computing system is configured to receive the analyte data from the first display device and share the analyte data with the second display device;

determining, by the first display device, that the first display device is unable to connect with the server computing system; and in response to determining that the first display device is unable to connect with the server computing system:

automatically initiating, by the first display device, a scan to detect one or more additional display devices in proximity to the first display device;

detecting, by the first display device and based on the scan, the second display device that is in proximity to the first display device, wherein the second display device is one of the one or more additional display devices;

in response to detecting the second display device, establishing, by the first display device, a communication link with the second display device; and transmitting the analyte data from the first display device to the second display device in order to display the analyte data and receive an alert that the one or more values of the analyte data were determined to exceed a first threshold or drop below a second threshold.

2. The computer-implemented method of claim 1, wherein detecting that the first display device is unable to connect with the server computing system comprises determining that a predefined amount of time has elapsed since receiving a message from the server computing system.

3. The computer-implemented method of claim 1, wherein detecting that the first display device is unable to connect with the server computing system comprises determining that the first display device has lost at least one of WiFi connectivity or cellular connectivity with the server computing system.

4. The computer-implemented method of claim 1, wherein the communication link is a Bluetooth communication link.

5. The computer-implemented method of claim 1, further comprising:
- presenting a list of the one or more additional display devices on a user interface of the first display device, wherein:
- the analyte data is analyte data of a patient,
- the second display device is determined, by the first display device, to be included in a predetermined list of devices of supporters having a predefined relationship with the patient;
- the predefined relationship includes a familial relationship; and
- the one or more additional display devices are not associated with a whitelist associated with the first display device.

6. The computer-implemented method of claim 1, wherein the analyte data comprises analyte data of a patient, and wherein the second display device is authorized by the patient to access the analyte data.

7. The computer-implemented method of claim 6, wherein the first display device maintains a whitelist associated with the first display device, the whitelist including the second display device, and wherein, in response to determining that the first display device is unable to connect with the server computing system, the first display device attempts to establish the communication link with the second display device based on the whitelist.

8. The computer-implemented method of claim 1, wherein, when the first display device is able to connect with the server computing system:
- the first display device obtains additional analyte data from the analyte monitoring device, and
- the first display device sends the additional analyte data to the server computing system so that the one or more additional display devices can access the additional analyte data via the server computing system.

9. A medical support system comprising:
- an analyte monitoring device generating analyte data; and
- a first display device comprising at least one processor and a memory storing executable instructions, which when executed by the at least one processor, perform an operation comprising:
  - obtaining the analyte data from the analyte monitoring device;
  - determining that one or more values of the analyte data exceed a first threshold or drop below a second threshold;
  - attempting to share the analyte data with a second display device separate from the first display device via a server computing system, where the server computing system is configured to receive the analyte data from the first display device and share the analyte data with the second display device;
  - determining that the first display device is unable to connect with the server computing system; and
  - in response to determining that the first display device is unable to connect with the server computing system:
    - automatically initiating a scan to detect one or more additional display devices in proximity to the first display device;
    - detecting, by the first display device and based on the scan, the second display device that is in proximity to the first display device, wherein the second display device is one of the one or more additional display devices;
    - in response to detecting the second display device, establishing a communication link with the second display device; and
    - transmitting the analyte data to the second display device in order to display the analyte data and receive an alert that the one or more values of the analyte data were determined to exceed a first threshold or drop below a second threshold.

10. The medical support system of claim 9, wherein detecting that the first display device is unable to connect with the server computing system comprises determining that a predefined amount of time has elapsed since receiving a message from the server computing system.

11. The medical support system of claim 9, wherein detecting that the first display device is unable to connect with the server computing system comprises determining that the first display device has lost at least one of WiFi connectivity or cellular connectivity with the server computing system.

12. The medical support system of claim 9, wherein the communication link is a Bluetooth communication link.

13. The medical support system of claim 9, wherein:
- the analyte data is analyte data of a patient, and
- the second display device is determined, by the first display device, to be included in a predetermined list of devices of supporters having a predefined relationship with the patient.

14. The medical support system of claim 9, wherein, when the first display device is able to connect with the server computing system:
- the first display device obtains additional analyte data from the analyte monitoring device, and
- the first display device sends the additional analyte data to the server computing system so that the one or more additional display devices can access the additional analyte data via the server computing system.

15. A first display device comprising:
- at least one processor; and
- a memory storing executable instructions, which when executed by the at least one processor, perform an operation comprising:
  - obtaining analyte data from an analyte monitoring device;
  - determining that one or more values of the analyte data exceed a first threshold or drop below a second threshold;
  - attempting to share the analyte data with a second display device separate from the first display device via a server computing system, where the server computing system is configured to receive the analyte data from the first display device and share the analyte data with the second display device;
  - determining that the first display device is unable to connect with the server computing system; and in response to determining that the first display device is unable to connect with the server computing system:

automatically initiating a scan to detect one or more additional display devices in proximity to the first display device;

detecting, by the first display device and based on the scan, the second display device that is in proximity to the first display device, wherein the second display device is one of the one or more additional display devices;

in response to detecting the second display device, establishing a communication link with the second display device; and transmitting the analyte data to the second display device in order to display the analyte data and receive an alert that the one or more values of the analyte data were determined to exceed a first threshold or drop below a second threshold.

16. The first display device of claim 15, wherein detecting that the first display device is unable to connect with the server computing system comprises determining that a predefined amount of time has elapsed since receiving a message from the server computing system.

17. The first display device of claim 15, wherein detecting that the first display device is unable to connect with the server computing system comprises determining that the first display device has lost at least one of WiFi connectivity or cellular connectivity with the server computing system.

18. The first display device of claim 15, wherein the one or more additional display devices are indicated on a whitelist associated with the first display device.

19. The first display device of claim 15, further comprising presenting a list of the one or more additional display devices on a user interface of the first display device.

20. The first display device of claim 19, further comprising receiving an indication of the second display device that has been selected from the list of the one or more additional display devices presented on the user interface of the first display device.

* * * * *